United States Patent
Sellinger et al.

(10) Patent No.: US 7,906,724 B2
(45) Date of Patent: Mar. 15, 2011

(54) N-TYPE CONJUGATED MATERIALS BASED ON 2-VINYL-4,5-DICYANOIMIDAZOLES AND THEIR USE IN ORGANIC PHOTOVOLTAICS

(75) Inventors: Alan Sellinger, Singapore (SG); Richard Yee Cheong Shin, Singapore (SG); Thomas Kietzke, Singapore (SG); Zhikuan Chen, Singapore (SG); Sundarraj Sudhakar, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 516 days.

(21) Appl. No.: 11/888,562

(22) Filed: Jul. 31, 2007

(65) Prior Publication Data
US 2009/0032106 A1    Feb. 5, 2009

(51) Int. Cl.
H01L 31/00 (2006.01)
B32B 27/32 (2006.01)
C07D 271/06 (2006.01)
C07D 285/14 (2006.01)
C07D 233/66 (2006.01)
C07D 233/90 (2006.01)

(52) U.S. Cl. ...... 136/263; 428/220; 548/126; 548/337.1

(58) Field of Classification Search .......... 548/100, 548/126, 337.1, 127, 300.1, 314.7; 136/263; 428/220
See application file for complete search history.

(56) References Cited

U.S. PATENT DOCUMENTS

| 6,517,958 | B1 | 2/2003 | Sellinger et al. |
| 6,861,091 | B2 | 3/2005 | Sellinger |
| 2005/0019602 | A1 | 1/2005 | Sellinger |
| 2006/0105491 | A1 | 5/2006 | Brabec et al. |
| 2006/0278890 | A1 | 12/2006 | Brabec et al. |
| 2007/0090371 | A1 | 4/2007 | Drechsel et al. |

FOREIGN PATENT DOCUMENTS

| EP | 1 508 925 A2 | 2/2005 |
| EP | 1 691 428 A2 | 8/2006 |
| EP | 1 736 476 A1 | 12/2006 |
| JP | 54112861 | * 9/1979 |
| JP | 7106613 A | 4/1995 |
| JP | 2007112046 | * 5/2007 |
| WO | WO 02/05971 A1 | 1/2002 |
| WO | WO 02/101838 A1 | 12/2002 |

OTHER PUBLICATIONS

Kietzke et al. "Effect of annealing on the characteristics of organic solar cells: polymer blends wtih a 2-vinyl-4,5-dicyanoimidazole derivative," Macromolecules, 40, 4424-4428, Jun. 2, 2007.*
Machine translation of JP2007112046, pub. May 10, 2007.*
Brabec et al., Plastic Solar Cells, Advanced Functional Materials, Feb. 14, 2001, pp. 15-26, vol. 11, Issue 1.

(Continued)

*Primary Examiner* — Jeffrey T Barton
*Assistant Examiner* — Allison Bourke
(74) *Attorney, Agent, or Firm* — Klarquist Sparkman, LLP

(57) ABSTRACT

There is provided novel n-type conjugated compounds based on 2-vinyl-4,5-dicyanoimidazole moieties conjugated via the vinyl group to an aromatic moiety. Also provided are thin films and photovoltaics comprising the novel compounds, as well as methods of synthesizing the compounds.

33 Claims, 16 Drawing Sheets
(12 of 16 Drawing Sheet(s) Filed in Color)

OTHER PUBLICATIONS

Cha, S.W. and Jin, J.I., Electroluminescence of LEDs consisting of two layers of Alq3 and high Tg, blue-light emitting branched compounds, Synthetic Metals, May 7, 2004, pp. 97-101, vol. 143, Issue 1.

Chan, H.S.O. and Ng, S.C., Synthesis, characterization and applications of thiophene-based functional polymers, Progress in Polymer Science, Nov. 1998, vol. 23, Issue 7, pp. 1167-1231.

D'Andrade, B.W. et al., Relationship between the ionization and oxidation potentials of molecular organic semiconductors, Organic Electronics, Feb. 2005, pp. 11-20, vol. 6, Issue 1.

Friend, R.H. et al., Electroluminescence in conjugated polymers, Nature, Jan. 14, 1999, pp. 121-128, vol. 397, No. 6715.

Greenham, N.C. et al., Efficient light-emitting diodes based on polymers with high electron affinities, Nature, Oct. 14, 1993, pp. 628-630, vol. 365, No. 6447.

Halls, J.J.M. et al., Efficient photodiodes from interpenetrating polyme networks, Nature, Aug. 10, 1995, pp. 498-500. vol. 376. No. 6540.

Hoppe, H. and Sariciftci, N.S., Morphology of polymer/fullerene bulk heterojunction solar cells, Journal of Materials Chemistry, 2006, pp. 45-61, vol. 16, Issue 1.

Hou, Q. et al., Novel red-emitting fluorene-based copolymers, Journal of Materials Chemistry, 2002 pp. 2887-2892, vol. 12, Issue 10.

Hughes, G. and Bryce, M.R., Electron-transporting materials for organic electroluminescent and electrophosphorescent devices, Journal of Materials Chemistry, 2005, pp. 94-107, vol. 15, Issue 1.

Johnson, D.M. and Rasmussen, P.G., An Improved Synthesis of 2-Vinyl-4,5-dicyanoimidazole and Characterization of Its Polymers, Macromolecules, Nov. 14, 2000, pp. 8597-8603, vol. 33, Issue 23.

Katz, H.E. et al., Synthetic Chemistry for Ultrapure, Processable, and High-Mobility Organic Transistor Semiconductors, Accounts of Chemical Research, May 2001, pp. 359-369, vol. 34, Issue 5.

Kietzke, T. et al., Efficient Polymer Solar Cells Based on M3EH-PPV, Chemistry of Materials, Dec. 27, 2005, pp. 6532-6537, vol. 17, Issue 26.

Kietzke, T. et al., Comparative Study of M3EH-PPV-Based Bilayer Photovoltaic Devices, Macromolecules, Jun. 13, 2006, pp. 4018-4022, vol. 39, Issue 12.

Kim, S.W. et al., 2.4-in. monochrome small molecular OLED display for mobile application, Current Applied Physics, Aug. 2002, pp. 335-338, vol. 2. Issue 4.

Kim, B.S. et al, Charge mobilities and luminescence characteristics of blue-light emitting bent carbazole trimers connected through vinylene linkers—effect of nitrile substituents, Synthetic Metals, Sep. 21, 2004, pp. 229-235, vol. 145, Issues 2-3.

Kulkarni, A.P. et al., Electron Transport Materials for Organic Light-Emitting Diodes, Chemistry of Materials. Nov. 16, 2004, pp. 4556-4573. vol. 16, Issue 23.

Densmore. C.G. and Rasmussen. P.G., New Acetylenic Monomers end Polymers from 4,5-Dicyanoimidazole, Macromolecules, Aug. 10, 2004, pp. 5900-5910, vol. 37, Issue 16.

Shin et al., N-Type Conjugated Materials Based on 2-Vinyl-4,5-dicyanoimidazoles and Their Use in Solar Cells, Chemistry of Materials, Apr. 17, 2007, pp. 1892-1894, vol. 19, No. 8.

Subrayan, R.P. and Rasmussen, P.G., High nitrogen chemistry: Synthesis and properties of N,N-bis(4,5-dicyano-1-methyl-2-Imidazoyl) cyanamide and N,N,N', N', N" N"-hexakis(4,5-dicyano-1-methyl-2-imidazoly)melamine. Tetrahedron, Jan. 8, 1999, pp. 353-358; vol. 55, Issue 2.

Thelakkat, M., Star-Shaped, Dendrimeric and Polymeric Triarylamines as Photoconductors and Hole Transport Materials for Electro-Optical Application, Macromolecular Materials and Engineering, Jul. 2002, pp. 442-461, vol. 287, Issue 7.

Littke, A.F. and Fu, G.C., A Versatile Catalyst for Heck Reactions for Aryl Chlorides and Aryl Bromides under Mild Conditions, Journal of the American Chemical Society, Jul. 25, 2001, pp. 6989-7000, vol. 123, Issue 29.

Li, J. et al., Poly(2,7-carbazole) and perylene tetracarboxydiimide; a promising donor/acceptor pair for polymer solar cells, Journal of Materials Chemistry, 2006, pp. 96-100, vol. 16, Issue 1.

Shin, W.S. et al., Effects of functional groups at perylene diimide derivatives on organic photovoltaic device application, Journal of Materials Chemistry, 2006, pp. 384-390, vol. 16, Issue 4.

Koster, L.J.A. et al., Ultimate efficiency of polymer/fullerene bulk heterojunction solar cells, Applied Physics Letters, Feb. 27, 2006, 093511 (3 pages), vol. 88, Issue 9.

\* cited by examiner

| Compound | $T_g$ (°C)[a] | $T_m$ (°C)[a] | $T_d$ (°C)[b] | UV-vis $\lambda_{max}$ (nm)[c] | PL $\lambda_{max}$ (nm)[c] | $\Phi$[d] | HOMO/LUMO (eV)[f] (bandgap) |
|---|---|---|---|---|---|---|---|
| 1 | 59 | 250 | 382 | 376 | 413 (sh), 437 | 0.56 | -6.05/-3.00 (3.05) |
| 2 | 60 | 257 | 328 | 355 | na | 0 | -6.47/-3.52 (2.95) |
| 3 | na | 208 | 402 | 369 | 417 (sh), 442 | 0.76 | -5.98/-2.84 (3.14) |
| 4 | na | 205 | 381 | 337, 448 | 516 | 0.48 | -6.06/-3.49 (2.57) |
| 5 | na | 266 | 400 | 390, 520 | 606 | 0.13[e] | -5.55/-3.44 (2.11) |
| 6 | na | 244 | 382 | 450 | 506, 541 | 0.19 | -5.59/-3.09 (2.50) |
| 7 | na | 238 | 387 | 390, 409 (sh) | 427, 453 | 0.74 | -5.82/-2.84 (2.98) |
| Compound | $T_g$ (°C)[a] | $T_m$ (°C)[a] | $T_d$ (°C)[b] | UV-vis $\lambda_{max}$ (nm)[c] | PL $\lambda_{max}$ (nm)[c] | $\Phi$[d] | HOMO/LUMO (eV)[f] (bandgap) |
| 8 | na | 226 | 410 | 321, 386 | 426, 455 (sh) | 0.05 | -5.47/-2.55 (2.92) |
| 9 | na | 257 | 414 | 331 | 397, 411 | 0.02 | -5.86/-2.72 (3.14) |
| 10 | na | 215 | 396 | 392 | 467, 496 | 0.57 | -5.85/-3.11 (2.74) |
| 11 | 89 | na | 393 | 362 | 445 | 0.09 | -5.87/-2.77 (3.10) |
| 12 | 72 | 221 | 371 | 365, 429 | na | 0 | -5.26/-3.21 (2.05) |
| 13 | 53 | 279 | 376 | 422 | 592 | 0.29 | -5.60/-3.27 (2.33) |
| 14 | 86 | na | 343 | 516 | 638 | 0.07[e] | -5.33/-3.42 (1.91) |

[a] Obtained from DSC measurement.
[b] Obtained from TGA measurement (temperature at 5% weight loss).
[c] Measured in a Toluene solution.
[d] Measured in a Toluene solution by using quinine sulfate as standard.
[e] Measured in a Toluene solution by using rhodamine 6G as standard.
[f] Calculated from CV data and UV-vis absorption spectral band edge (in cases where only the ol6idation or reduction cycle could be obtained from CV). na = not detected.

FIGURE 14

N-TYPE CONJUGATED MATERIALS BASED ON 2-VINYL-4,5-DICYANOIMIDAZOLES AND THEIR USE IN ORGANIC PHOTOVOLTAICS

FIELD OF THE INVENTION

The present invention relates generally to organic materials, useful for production of organic photovoltaics, and particularly to materials having one or more 2-vinyl-4,5-dicyanoimidazole moiety.

BACKGROUND OF THE INVENTION

Organic light-emitting diodes (OLEDs), organic field-effect transistors (OFETs), and organic solar cells (also referred to as organic photovoltaics or OPVs) based on π-conjugated materials have been extensively studied since the early 1990s because of their low-cost processing, relatively simple packaging, and compatibility with flexible substrates (Friend et al., Nature 1999, 397, 121; Katz et al., Acc. Chem. Res. 2001, 34, 359; and Brabec et al., Adv. Funct. Mater. 2001, 11, 15).

More specifically, OPVs come with the promise of efficient conversion of sunlight into direct usable electrical energy at a much lower cost than the traditional silicon based solar cells. It is known that for efficient energy conversion in OPVs, a mixture of at least two (sometimes more) organic materials are needed: at least one material that can act as an electron donor (p-type) and at least one material that can act as electron acceptor (n-type).

Materials research in OPVs since the mid-1990s has focused primarily on the development of donor materials. As a result, there are many more organic donor materials commercially available than organic acceptor materials. For example, the most widely investigated organic semiconductors are donor materials based on aromatic amines and thiophene materials (Katz et al., Acc. Chem. Res. 2001, 34, 359; Chan and Ng, Prog. Polym. Sci. 1998, 23, 1167; and Thelakkat, Macromol. Mater. Eng. 2002, 287, 442).

In contrast, research in electron acceptors has substantially lagged behind. Work in this area has primarily focussed on perylene and fullerene materials, which in general are relatively difficult to work with in terms of synthesis of the materials. The field of high-performance organic electronic devices will advance significantly with the development of new organic n-type semiconductors with high electron mobilities and controllable HOMO and LUMO energy levels (Greenham, et al., Nature 1993, 365, 628; Kulkarni et al., Chem. Mater. 2004, 16, 4556; and Hughes and Bryce, J. Mater. Chem. 2005, 15, 94).

For example, OPVs incorporating heterojunctions of p- and n-type conjugated materials demonstrate much better performance than devices incorporating only a single type of material, since the heterojunction promotes dissociation of photogenerated excitons into free charge carriers that in turn create the desired photovoltaic effect to generate electricity (Brabec et al., Adv. Funct. Mater. 2001, 11, 15; Halls et al., Nature 1995, 376, 498; Hoppe and Sariciftci, J. Mater. Chem. 2006, 16, 45; and Kietzke et al., Macromolecules 2006, 39, 4018).

Currently, perylenes and fullerenes are the dominant n-type material used in OPVs. The chemistry of these compounds is relatively well known, with little room for new developments. Furthermore, production of these materials tends to be very expensive, especially in the case of fullerene based materials. Perylenes are typically insoluble, meaning that often only vacuum deposition of these compounds is possible. Since the mid-1990s, fullerene compounds have been optimized for use in solution processable organic solar cells, providing power conversion efficiencies in the range of 2-5% when combined with selected commercial donor materials. Despite this, fullerenes tend to have low absorption coefficients in the visible range, are difficult to synthesize, and have low open circuit voltage in blend devices.

Accordingly, there is a need for production of alternative n-type organic materials useful for production of efficient electronic devices, including OPVs.

SUMMARY OF THE INVENTION

The present invention relates to a new class of n-type conjugated compounds.

Conveniently, these new n-type compounds may be synthesized by the palladium Heck coupling of 2-vinyl-4,5-dicyanoimidazole with selected functionalized aromatic compounds. The presently described n-type compounds may be readily prepared in high yields from one-step reactions using commercially available materials and are solution processable.

Organic photovoltaic cells incorporating the novel materials as an electron acceptor can be produced having relatively high external quantum efficiencies, making these novel materials useful in the production of efficient and cost-effective organic photovoltaic cells.

Thus, in one aspect, the present invention provides a compound of formula I:

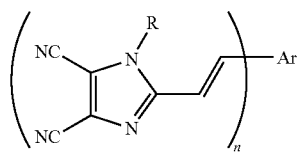

wherein Ar is an aryl or heteroaryl group having from 5 to 100 backbone atoms, R is a $C_1$ to $C_{30}$ branched, unbranched or cyclic alkyl or heteroalkyl group, and n is an integer from 1 to 10.

In another aspect, there is provided a thin layer comprising a compound as described herein.

In another aspect, there is provided a device comprising an anode, a cathode and an electron acceptor material comprising a compound as described herein, the electron acceptor material disposed between the anode and the cathode.

In a further aspect, there is provided a method of synthesizing a compound as described herein, the method comprising reacting 1-R-vinzene with a bromoaromatic compound in the presence of a palladium catalyst and a base, wherein the bromoaromatic compound has from 5 to 100 backbone atoms and R is a $C_1$ to $C_{30}$ branched, unbranched or cyclic alkyl or heteroalkyl group.

Other aspects and features of the present invention will become apparent to those of ordinary skill in the art upon review of the following description of specific embodiments of the invention in conjunction with the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee. In the figures, which illustrate, by way of example only, embodiments of the present invention:

FIG. 14 is a table of physical properties of the vinazene oligomers 1 to 14;

DETAILED DESCRIPTION

Figure 1:
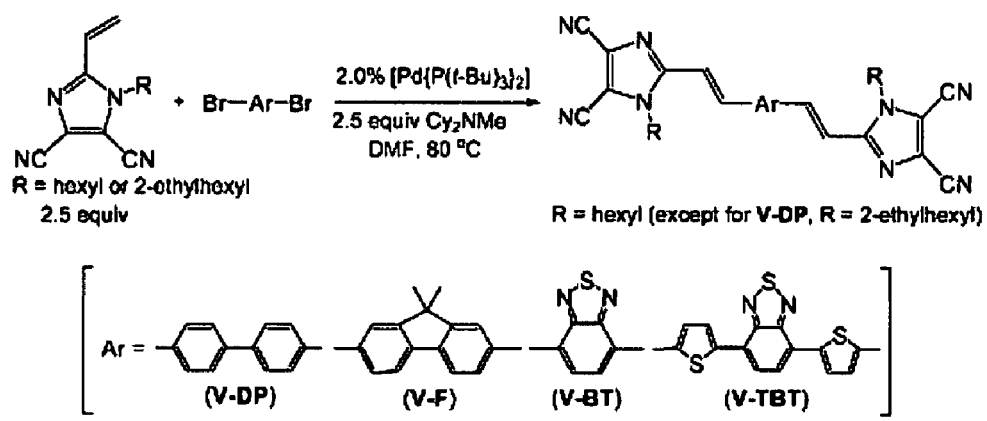
FIG. 1 is a schematic of Heck couplings of aryl dibromides and 1-alkylvinazene to produce particular embodiments of compounds of the present invention.

Presented here are novel n-type conjugated compounds based on 2-vinyl-4,5-dicyanoimidazoles and the resultant organic electronic devices incorporating such compounds. The compounds are easily synthesized and are solution processable. Accordingly, electronic devices incorporating the novel compounds may be easily manufactured, including using solution based techniques such as inkjet printing, dip and/or spin coating, and screen printing, to name a few.

2-vinyl-4,5-dicyanoimidazole (trivial name vinazene) has previously been used as a monomer or comonomer in the preparation of imidazole-containing polymers and as high-nitrogen-containing heterocyclic molecules having reduced flammability (Johnson and Rasmussen, *Macromolecules* 2000, 33, 8597; Subrayan and Rasmussen, *Tetrahedron* 1999, 55, 353; and Rasmussen et al., *Macromolecules* 2004, 37, 5900).

However, the Heck chemistry of vinazenes or the use of resultant compounds for application in organic electronic devices has not previously been reported. As fullerene derivatives are expensive and involve complicated syntheses, vinazene derivatives are an attractive alternative for low-cost electron acceptor materials. Furthermore, vinazene derivatives are much easier to prepare than cyano-PPV derivatives, which are also used as acceptors in organic solar cells (Kietzke et al., *Chem. Mater.* 2005, 17, 6532).

The present compounds are synthesized from one or more vinazene molecules conjugated with an aromatic molecule via the vinyl group on each vinazene molecule.

The vinyl group of the vinazene provides the reactive site for chemically linking this moiety to selected aromatics via the Heck reaction. The nitrogen at the 1 position provides a site for alkylation, which is used to tune the solubility of the present compounds. The selected aromatics are used to tune the electronic properties of the novel compounds. All together, this provides a very strategic methodology for the preparation of useful n-type materials for application in organic electronics, particularly including organic solar cells.

The resulting conjugated vinazene-aromatic molecule contains a conjugated system of overlapping π-bonds along the length of the molecule, contributed by the dicyanoimidazole unit and vinyl groups from the vinazene moieties and the aromatic ring or rings from the aromatic moiety.

The cyano and imidazole groups of the novel 2-vinyl-4,5-dicyanoimidazole compounds are strong electron withdrawing groups, providing n-type characteristics to the compounds. The electron deficient properties of the present compounds, together with their strong absorption capabilities in the visible range, make them good candidates as acceptor materials in organic electronic devices.

The term "conjugated" as used herein in reference to the backbone of a molecule refers to a molecule having two or more double and/or triple bonds in the main chain of the molecule, each double or triple bond being separated from the next consecutive double or triple bond by a single bond so that π orbitals overlap not only across the double or triple bond, but also across adjacent single bonds located between adjacent double and/or triple bonds.

Thus, there is provided a compound of formula I:

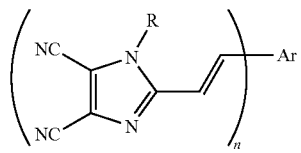

Ar in the above formula is any aromatic group, including a heteroaromatic group.

As will be understood, an aromatic group is a cyclic group having 4 m+2π electrons, where m is an integer equal to or greater then 0. As used herein, "aromatic" is used interchangeably with "aryl" to refer to an aromatic group, regardless of the valency of aromatic group. Thus, aryl refers to monovalent aromatic groups, bivalent aromatic groups and higher multivalency aromatic groups.

A heteroaromatic group is an aromatic group containing one or more heteroatoms, such as N, O, S, Se, Si or P. As used herein, "heteroaromatic" is used interchangeably with "heteroaryl", and a heteroaryl group refers to monovalent aromatic groups, bivalent aromatic groups and higher multivalency aromatic groups containing one or more heteroatoms.

Thus, in the present description, Ar includes hydrocarbon aromatic groups, for example benzene, fluorene, naphthalene, anthracene, pyrene, perylene, tetracene, and pentacene. Ar also includes heteroaromatic groups, including thiophene, furan, pyrole, silole, pyridine, benzothiadiazole, imidazole, thiazole, and triazine. The Ar group may be substituted or unsubstituted, including with fluorine, and may consist of two or more aromatic groups conjugated together so as to maintain a conjugated π bond system.

In certain embodiments, the aryl group may have from 5 to 100 backbone carbon and hetero atoms, from 5 to 60 backbone carbon and hetero atoms, from 5 to 50 backbone carbon and hetero atoms, from 5 to 30 backbone carbon and hetero atoms, or from 5 to 20 backbone carbon and hetero atoms.

In particular embodiments, Ar comprises phenyl, nitro-substituted phenyl, alkoxy-substituted phenyl, biphenyl, benzothiadiazolyl, thiophenyl-benzothidiazolyl-thiophenyl, thiophenyl, thienothiophenyl, bithiophenyl, 9,9-dialkylfluorenyl, N-alkylcarbozolyl, dibenzothiophenyl, naphthalyl, binaphthalyl, azulenyl, anthracenyl, tetracenyl, indenyl, pyrenyl or perylenyl. In a particular embodiment, Ar comprises benzothiadiazolyl.

In particular embodiments, Ar consists of phenyl, nitro-substituted phenyl, alkoxy-substituted phenyl, biphenyl, benzothiadiazolyl, thiophenyl-benzothidiazolyl-thiophenyl, thiophenyl, thienothiophenyl, bithiophenyl, 9,9-dialkylfluorenyl, N-alkylcarbozolyl, dibenzothiophenyl, naphthalyl, binaphthalyl, azulenyl, anthracenyl, tetracenyl, indenyl, pyrenyl or perylenyl. In one particular embodiment, Ar consists of benzothiadiazolyl.

In the above formula I, n is an integer equal to or greater than 1. Thus, compounds of the present invention contain at least one vinazene moiety, and may contain more than one vinazene moiety, depending on the reactivity of the original aromatic compound used to synthesize the present compounds. In particular embodiments, n is an integer from 1 to 10 inclusive, or from 1 to 4 inclusive. In particular embodiments, n is equal to 2.

R in the above formula I may be a $C_1$ to $C_{30}$ branched, unbranched or cyclic alkyl group, which may include one or more heteroatoms such as N, O, S, Se, Si or P in the backbone, and which may be substituted or unsubstituted, including with fluorine. As used herein, "fluorinated alkyl" refers to a branched, unbranched or cyclic alkyl group in which at least one hydrogen atom has been replaced with a fluorine atom.

Where the compound as presently described contains two or more vinazene moieties (i.e. n is equal to or greater than 2), R on each vinazene moiety is independently selected as described above. Thus, R can be the same or different on different vinazene compounds within the same molecule.

In particular embodiments, R comprises branched hexyl, unbranched hexyl, 2-ethylhexyl, cyclohexylmethyl, or fluorinated alkyl. In particular embodiments, R consists of branched hexyl, unbranched hexyl, 2-ethylhexyl, cyclohexylmethyl, or fluorinated alkyl. In particular embodiments, R comprises hexyl, 2-ethylhexyl or a mixture thereof. In other embodiments, R consists of hexyl, 2-ethylhexyl or a combination of hexyl and 2-ethylhexyl.

In certain embodiments of the present invention, n is equal to 2. Thus, there are presented compounds of formula Ia:

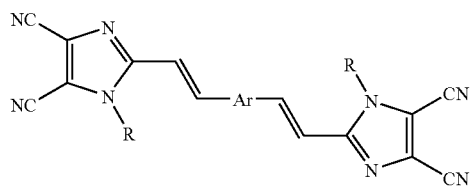

Ar and R are as defined above.

In particular embodiments of compounds of formula Ia, Ar comprises one or more of the following bivalent Ar groups, or consists of one of the following bivalent Ar groups:

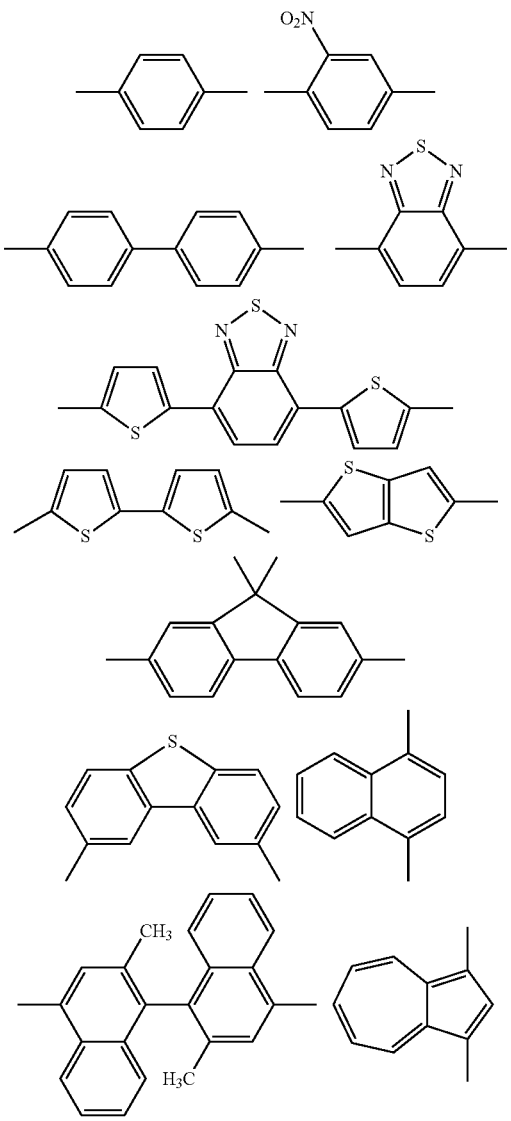

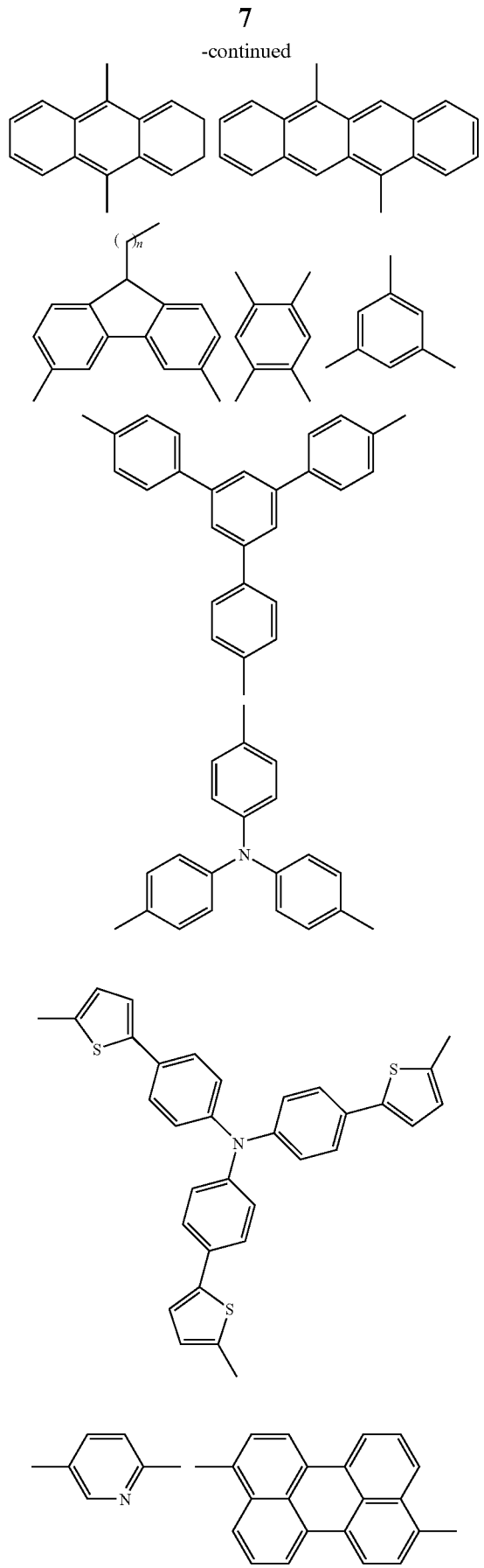

It will be appreciated that while the above Ar groups are depicted as bivalent for inclusion in compounds of formula Ia (since n=2), the corresponding suitable monovalent or multivalent Ar groups may be included in compounds of formula I when n is equal to 1, 3 or higher.

In particular embodiments of compounds of formula Ia, each R independently comprises hexyl or 2-ethylhexyl. In particular embodiments of compounds of formula Ia, each R independently is hexyl or 2-ethylhexyl.

As stated above, the present compounds are electron deficient, and thus function as electron acceptor, or n-type, materials. The extended π molecular orbitals, when unfilled or when only partially filled with electrons, provide channels across the molecule for transport of electrons when the molecule is placed under a voltage bias. Several such extended π orbitals can form across a conductive organic compound, each having different structure and energy levels. The molecular orbital having the lowest energy level is often an effective path for transport of extra electrons.

The energy level of the HOMO (highest occupied molecular orbital) and the LUMO (lowest unoccupied molecular orbital) of the present compounds can be primarily tuned through selection of a particular Ar group. Thus, the bandgap (difference in energy level between the LUMO and HOMO) can be varied with the Ar group, and selected based on desired application, and considerations such as the energy levels of the p-type donor material used in an organic electronic device.

For example, values ranging from −5.50 to −6.10 eV (HOMO) and −2.80 to −3.60 eV (LUMO) can be obtained in certain embodiments of the present compounds. As will be understood, and as described in the following examples, HOMO and LUMO levels can be measured using standard methods of cyclic voltammography.

Selection of the R group can be used to adjust the solubility of the compounds in particular solvents. Increased solubility can improve the phase separation of the compound into the appropriate organic phase during manufacture of a device, leading to higher efficiencies of the resulting device. It will be understood that to improve solubility in an apolar solvent, increased alkyl chain length and increased alkyl branching will provide more apolar surface to the compound.

The compounds described herein possess photophysical properties that make them suitable as electron acceptor (n-type) materials in organic electronic devices, including solar cells and photodetectors. The compounds show strong absorption and emission ultraviolet and visible ranges, for example in the 330-520 nm and 410-610 nm ranges, respectively. The molecules exhibit high photoluminescence (PL) quantum efficiencies and emission from blue to red.

The present compounds exhibit relatively high thermal stability (e.g., greater than 381° C.) under $N_2$, and high melting temperatures. For the exemplified compounds described in the following examples, all but two of the compounds melt above 205° C.

Thus, the presently described compounds of formula I (including formula Ia) conveniently are solution processable, are easy to synthesize in high purity, possess strong absorption in the visible region, and provide a mechanism for tuning the HOMO and LUMO energy levels to suit the corresponding energy levels of the different available electron donating materials.

The present compounds can be readily synthesized using known organic chemistry methods.

For example, Heck coupling chemistry can be used to prepare the present compounds in high yields using vinazene compounds and suitably substituted bromoaromatic compounds, including as described in the following examples. Heck coupling involves a palladium catalyst to achieve C—C coupling between an aryl halide and an activated alkene in the presence of a base.

It will be appreciated that depending on the number of vinazene moieties to be included in the final desired compound of formula I, the aromatic compound will be brominated at one or more positions on the aromatic compound. Thus, one or more hydrogens on an aromatic compound are substituted with bromine prior to reaction in a Heck coupling reaction with a suitably substituted vinazene. The resultant compound of formula I will comprise a central Ar core, linked to a vinazene moiety through the vinyl group of the vinazene at each position at which the aromatic compound was originally brominated.

An exemplary synthesis mechanism for synthesis of particular compounds using dibromoaromatic compounds and particular vinazene compounds is set out in the schematic in FIG. 1.

Thus, there is presently provided a method of synthesizing a compound of formula by reacting 1-R-vinzene with a bromoaromatic compound in the presence of a palladium catalyst and a base, where the bromoaromatic compound has from 5 to 100 backbone atoms and R is a $C_1$ to $C_{30}$ branched, unbranched or cyclic alkyl or heteroalkyl group, as described above. As will be appreciated, a bromoaromatic compound is an aromatic compound as described above, in which one or more hydrogens have been replaced with bromine atoms, such that when the bromine atoms are replaced with a vinyl group of a vinazene moiety, the final compound is conjugated along its backbone.

For example, in one embodiment, 2.5 molar equivalents of 1-R-vinazene, derivatized with the appropriate R substituent, is reacted with one molar equivalent of the appropriate dibromoaromatic compound at approximately 80° C. The reaction is carried out in a suitable solvent, such as dimethylfommamide, using bis(tri-t-butylphosphine)-palladium(0) [Pd[P(t-Bu)$_3$]$_2$] as catalyst and 2.5 molar equivalents of dicyclohexylmethylamine (Cy$_2$NMe) as base/HBr scavenger. The products can be isolated by precipitation in ethanol followed by recrystallization.

In various embodiments, the dibromoaromatic compound comprises 1,4-dibromobenzene, 1,4-dibromo-2-nitrobenzene, 4,4'-dibromobiphenyl, 4,7-dibromo-2,1,3-benzothiadiazole, 4,7-bis(5-bromo-2-thienyl)-2,1,3-benzothiadiazole, 5,5'-dibromo-2,2'-bithiophene, 2,7-dibromo-9,9'-dimethylfluorene, N-hexyl-3,6-dibromocarbazole, 3,6-dibromodibenzothiophene, 1,4-dibromonaphthalene, 4,4'-dibromo-2, 2'-dimethyl-1,1'-binaphthalyl, 1,3-dibromoazulene, 9,10-dibromoanthracene or 5,11-dibromotetracene.

Vinazene is commercially available, or may be synthesized as described in Johnson and Rasmussen, *Macromolecules* 2000, 33, 8597. If the vinazene is to be derivatized with an alkyl group, alkylation at the 1 position may be achieved using standard methods, as described in the following examples. For example, a halo-alkane is refluxed with vinazene in a suitable aprotic solvent, such as acetone or DMF, in the presence of anhydrous $K_2CO_3$. The solution is filtered and solvent is removed. The oily residue is mixed with water and extracted from the aqueous layer with ethyl acetate. The organic layer is dried and solvent removed. The resulting oily residue is recrystallized in various solvents and solvent combinations, including for example ethanol.

In various embodiments, the 1-R-vinazene comprises 1-hexylvinazene, 1-2-ethylhexylvinazene or 1-cyclohexylmethylvinazene, or a combination thereof.

As stated above, the present photophysical and electron deficient properties of the present compounds of formula I make the compounds suitable for use in organic electronic devices, including bipolar transistors, integrated circuits, photovoltaic devices, solar cells, photodetectors and light emitting diodes. The optoelectronic properties of the compounds, such as absorbance, photoluminescence and HOMO-LUMO energy levels, can be easily tuned over a wide range by simply changing the central aromatic segments. The widely tunable energy levels and bandgaps of the present compounds make these materials attractive for potential application as emissive and/or electron-transporting materials in organic electronic devices, and may be used to create an n-type layer or p-n junctions in such a device.

The present compounds are suitable for solution processing, thus allowing for production of a thin film containing the compounds, for inclusion in an organic electronic device. Thus, in one aspect there is provided a thin film comprising a compound of formula I.

The thin film is a layer comprising a compound of formula I as described above, which may be formed to be in the order of from about 0.1 to about 1000 nm thick, from about 1 to about 500 nm thick, from about 5 to about 250 nm thick, or from about 5 to about 100 nm thick.

When used in a solar cell, the thin film may constitute the photoactive layer of the solar cell, and thus may further comprise a suitable p-type electron donor material. For example, the donor material may comprise regioregular poly(3-hexylthiophene-2,5-diyl) (P3HT), regioregular poly(3-ocylthiophene-2,5-diyl) (P3OT), regioregular poly(quarterthiphene) (PQT), a-poly(phenylene ethynylene)-poly (phenylene vinylene) (A-PPE-PPV), poly[2-methoxy-5-(2'-ethyl-hexyloxy)-1,4-phenylene vinylene] (MEH-PPV), or poly[2-methoxy-5-(3,7-dimethyloctyloxy)-1,4-phenylenevinylene] (MDMO-PPV).

The thin film may be formed on a suitable substrate, which may be any solid substrate, including indium tin oxide (ITO) coated glass or plastic, fluorine tin oxide (FTO) coated glass or plastic, quartz, glass, mica, a plastic substrate such as polyethylene terephthalate or polycarbonate, paper, metal, or silicon. The thin film may also be layered onto another layer when forming a multilayered device, or onto an electrode.

To form the thin film, the compound of formula (I) and any additional film components may be dissolved in a suitable organic solvent. Suitable solvents include chloroform, toluene, a xylene, ethyl benzoate, methyl benzoate, 1,1,2,2-tetrachloroethane, THF, dioxane, chlorobenzene, dichlorobenzenes, mesitylene and mixtures of the aforesaid solvents.

The thin film may be formed on a suitable surface using standard deposition or coating methods including solution coating. Solution coating includes spin coating, casting, microgravure coating, gravure coating, bar coating, roll coating, wire bar coating, dip coating, spray coating, screen printing, flexo printing, offset printing and inkjet printing.

The compounds of formula (I) and thin films containing such compounds may be used to construct solar cells. The compounds of formula (I) and thin films containing such compounds may form the electron acceptor in the photoactive layer in an organic photovoltaic cell. Such devices and layers are known in the art.

Thus, in another aspect, there is provided a device comprising a compound of formula (I) or a thin film comprising a compound of formula (I).

Figure 2:
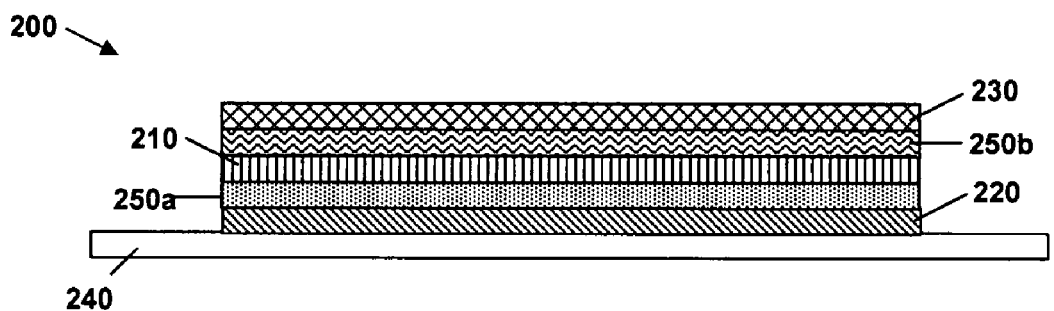
FIG. 2 is a representation of an electronic device incorporating a compound of formula I as an electron acceptor material.

In one embodiment, with reference to FIG. 2, device 200 comprises a photoactive layer 210 comprising a compound of formula (I) as an electron acceptor. The photoactive layer 210 further includes an electron donor, as described above.

Active layer 210 is disposed between cathode 220 and anode 230. In certain embodiments, photoactive layer 210 is from about 5 to about 100 nm thick.

The anode 230 is any material capable of conducting holes and injecting them into organic layers. Anode 230 may be gold, silver, fluorine tin oxide (FTO) or indium tin oxide (ITO), or conductive polymer layers. The anode 230 may be reflective, transparent, semi-transparent or translucent. In certain embodiments, the anode is transparent material such as ITO.

Cathode 220 is any material capable of conducting electrodes and injecting them into organic layers. Cathode 220 may be a low work function metal or metal alloy, including, for example, barium, calcium, magnesium, indium, aluminum, ytterbium, silver, a calcium:silver alloy, an aluminum:lithium alloy, or a magnesium:silver alloy, such as, for example an alloy wherein the atomic ratio of magnesium to silver is about 10:1 (U.S. Pat. No. 6,791,129) or an alloy where the atomic ratio of lithium to aluminum is about 0.1:100 to about 0.3:100 (Kim et al. (2002) *Curr. Appl. Phys.* 2(4):335-338; Cha et al (2004) *Synth. Met.* 143(1): 97; Kim et al (2004) *Synth. Met.* 145(2-3): 229). The cathode 230 may be a single layer or have a compound structure. Cathode 230 may comprise layers of lithium fluoride, aluminium and silver. The cathode 230 may be reflective, transparent, semi-transparent or translucent.

In certain embodiments, one or more of the anode and the cathode may be deposited on a support 240, which may be transparent, semi-transparent or translucent. Support 240 may be rigid, for example quartz or glass, or may be a flexible polymeric substrate. Examples of flexible transparent semi-transparent or translucent substrates include, but are not limited to, polyimides, polytetrafluoroethylenes, polyethylene terephthalates, polyolefins such as polypropylene and polyethylene, polyamides, polyacrylonitrile and polyacrionitrile, polymethacrylonitrile, polystyrenes, polyvinyl chloride, and fluorinated polymers such as polytetrafluoroethylene.

The device may optionally comprise an additional layer such as a smoothing layer 250 between the photoactive layer 210 and the anode 220 (250a), the cathode 230 (250b) or both. The smoothing layer 250 may be a poly(ethylene dioxytiophene)/polystyrene sulfonic acid (PEDOT:PSS) layer or Ca. The smoothing layer may be from about 20 nm to about 50 nm.

In a particular embodiment, device 200 comprises the following layers: glass/ITO/PEDOT:PSS/active layer/Ca/Ag, in which the photoactive layer is formed from 5.0 mg/mL of a compound of formula I and 5.0 mg/mL P3HT in chloroform.

The devices of the present invention demonstrate photoresponses in the range from 300 to 650 nm, with external quantum efficiencies exceeding 18% for particular embodiments. The photo-response resembles the absorbance of the photoactive layer, demonstrating that both donor materials and acceptor materials contribute equally to the photocurrent.

The above-mentioned devices may be prepared by layering the relevant layers on top of one another. The layers may be prepared by methods known in the art, including solution coating techniques mentioned above. Solution coating steps may be carried out in an inert atmosphere, such as, for example, under nitrogen gas. Alternatively, layers may be prepared by thermal evaporation or by vacuum deposition. Metallic layers may be prepared by known techniques, such as, for example, thermal or electron-beam evaporation, chemical-vapour deposition or sputtering.

The solar cells have been described above with a thin film comprising the electron donor material and electron acceptor material. However, it will be appreciated that the present compounds can be used to form devices in which the n-type electron acceptor material is in a separate layer from the p-type electron donor material.

The solar cell devices described herein may be used in stacked solar cells, in which two or more solar cells are stacked in a single device, for example as described in published patent application US 20070090371.

EXAMPLES

Example 1

Experimental Section

General Description: All commercially available materials were used as received unless noted otherwise. Cy$_2$NMe was distilled prior to use. 4,7-bis(5-bromo-2-thienyl)-2,1,3-benzothiadiazole was prepared according to literature procedures (Hou, Q.; Xu, Y.; Yang, W.; Yuan, M.; Peng, J.; Cao, Y. *J. Mater. Chem.* 2002, 10, 2887). All reactions were carried out using Schlenk techniques in an argon or nitrogen atmosphere with anhydrous solvents.

Instruments: $^1$H, and $^{13}$C NMR data were performed on a Bruker DPX 400 MHz spectrometer with chemical shifts referenced to CDCl$_3$ or C$_4$D$_8$O. Matrix assisted laser desorption/ionization time-of-flight (MALDI-TOF) mass spectra were obtained on a Bruker Autoflex TOF/TOF instrument using dithranol as a matrix and silver trifluoroacetate as an ionizing salt when necessary. Differential scanning calorimetry (DSC) was carried out under nitrogen on a DSC Q100 instrument (scanning rate of 10° C.·min$^{-1}$). Thermal gravimetric analysis (TGA) was carried out using TGA Q500 instrument (heating rate of 10° C.·min$^{-1}$). Cyclic voltammetry experiments were performed using an Autolab potentiostat (model PGSTAT30) by Echochimie. All CV measurements were recorded in dichloromethane with 0.1 M tetrabutylammonium hexafluorophosphate as supporting electrolyte (scan rate of 100 mV·s$^{-1}$). The experiments were performed at room temperature with a conventional three electrode configuration consisting of a platinum wire working electrode, a gold counter electrode, and a Ag/AgCl in 3 M KCl reference electrode. The measured potentials were converted to SCE (saturated calomel electrode) and the corresponding electron affinity (EA) values, to estimate the LUMO, were derived from the onset potential, based on −4.4 eV as the SCE energy level relative to vacuum (EA=E'$_{onset}$+ 4.4 eV) (Kulkarni et al., Chem. Mater. 2004, 16, 4556). UV-Vis spectra were recorded on a Shimadzu model 2501-PC UV-VIS spectrometer and the UV-vis absorption spectroscopic onset was used to calculate the bandgap. Photoluminescence (PL) spectra were measured on a Perkin-Elmer (LS50B) spectrofluorimeter.

Alkyl vinazene: To a solution of vinazene (1.00 g, 6.9 mmol) in 15 mL acetone was added anhydrous $K_2CO_3$ (1.40 g, 10.1 mmol) and 1-iodohexane (1.40 mL, 9.5 mmol). The solution was refluxed for 24 h, filtered and solvent removed under vacuum. Water (30 mL) was then added to the oily residue and the aqueous layer was extracted three times with 50 mL aliquots of ethyl acetate. The organic layer was dried over magnesium sulfate and the solvent removed under vacuum. The oily residue was recrystallised in EtOH to give pale yellow crystalline solids (1.42 g, 90% yield) after 24 h at 4° C. $^1$H NMR (CDCl$_3$): δ 0.90 (t, 3H, J=6.8 Hz), 1.33 (unresolved m, 6H), 1.80 (q, 2H, J=6.8 Hz), 4.11 (t, 2H, J=7.2 Hz), 5.82 (t, 1H, J=6.4 Hz), 6.52 (d, 2H, J=6.0 Hz). $^{13}$C NMR (CDCl$_3$): δ 14.0, 22.4, 26.1, 30.7, 31.1, 46.7, 108.5, 111.9, 112.3, 120.2, 122.5, 126.6, 149.4. The analogue 1-(2-ethylhexyl)vinazene was synthesized using DMF as solvent. After stirring for 24 h at 80° C., the solution was filtered and DMF removed under vacuum. The oily residue was purified by column chromatography (silica gel, 25% ethyl acetate in hexane as eluent). A pale yellow oil was obtained after solvent removal. The oil solidified upon cooling at 4° C. for 24 h to give the product as a cream colored solid (34% yield). $^1$H NMR (CDCl$_3$): δ 0.89 (t, 3H, J=6.4 Hz), 0.92 (t, 3H, J=7.6 Hz), 1.20-1.42 (m, 8H), 1.80 (septet, 1H, J=6.4 Hz), 3.98 (d, 2H, J=7.6 Hz), 5.81 (dd, 1H, J=8.4, 3.6 Hz), 6.45-6.55 (m, 2H). $^{13}$C NMR (CDCl$_3$): δ 10.6, 13.9, 22.9, 23.8, 28.4, 30.4, 41.0, 50.7, 108.7, 111.9, 112.9, 120.5, 122.6, 126.5, 149.8.

Procedure for Heck reactions: In a glovebox, the aryl halide, Cy$_2$NMe, Pd[P(t-Bu)$_3$]$_2$, DMF, and the olefin (alkyl vinazene) were added to an oven-dried Schlenk flask equipped with a stir bar. The Schlenk flask was taken out of the glove box, connected to the nitrogen line, and the reaction mixture was stirred at 80° C. for 20 h. At the end of the reaction, the reaction mixture was cooled to room temperature and filtered over a glass sinter (Por. 4). Ethanol was added to the filtrate while stirring to precipitate out the product which was collected and washed with EtOH and then hexane. The product obtained was then recrystallized from DMF/EtOH or THF/EtOH at 4° C.

V-DP: Using 4,4'-dibromobiphenyl (125 mg, 0.40 mmol), 1-ethylhexylvinazene (256 mg, 1.0 mmol), Cy$_2$NMe (0.214 mL, 1.0 mmol), Pd[P(t-Bu)$_3$]$_2$ (4.1 mg, 0.008 mmol), and DMF (2 mL). After workup, the product was obtained as yellow solids (108 mg, 41% yield). $^1$H NMR (CDCl$_3$): δ 0.91 (t, 6H, J=6.0 Hz), 0.98 (t, 6H, J=7.2 Hz), 1.32-1.46 (m, 16H), 1.86 (unresolved m, 2H), 4.07 (d, 4H, J=7.2 Hz), 6.81 (d, 2H, J=15.6 Hz), 7.63 (d, 4H, J=8.0 Hz), 7.69 (d, 4H, J=8.0 Hz), 7.90 (d, 2H, J=15.6 Hz). $^{13}$C NMR (CDCl$_3$): δ 10.8, 14.1, 23.0, 23.9, 28.6, 30.4, 41.2, 50.5, 108.8, 110.5, 112.0, 112.8, 122.6, 127.7, 128.3, 134.5, 139.7, 141.7, 150.3. Anal. Calcd for $C_{42}H_{46}N_8$: C, 76.10; H, 6.99; N, 16.90. Found: C, 76.04; H, 6.82; N, 16.99. MALDI-TOF-MS (dithranol) m/z: 663 (M+H); calcd. for $C_{42}H_{46}N_8$=662.

V-BT: Using 4,7-dibromo-2,1,3-benzothiadiazole (88 mg, 0.30 mmol), 1-hexylvinazene (171 mg, 0.75 mmol), Cy$_2$NMe (0.161 mL, 0.75 mmol), Pd[P(t-Bu)3]2 (3.1 mg, 0.006 mmol), and DMF (2 mL). After workup, the product was obtained as an orange solid (155 mg, 88% yield). $^1$H NMR (CDCl$_3$): δ 0.90 (t, 6H, J=7.2 Hz), 1.37 (unresolved m, 12H), 1.95 (q, 4H, J=7.2 Hz), 4.30 (t, 4H, J=7.2 Hz), 7.74 (s, 2H), 8.06 (d, 2H, J=15.6 Hz), 8.33 (d, 2H, J=15.6 Hz). $^{13}$C NMR (CDCl$_3$): δ14.0, 22.5, 26.2, 30.8, 31.2, 46.9, 108.6, 111.9, 112.7, 117.4, 123.2, 129.4, 132.5, 135.5, 150.2, 153.8. Anal. Calcd for $C_{32}H_{32}N_{10}S$: C, 65.28; H, 5.48; N, 23.79; S, 5.45. Found: C, 64.75; H, 5.37; N, 24.06; S, 5.19. MALDI-TOF-MS (dithranol) m/z: 589 (M+H); calcd. for $C_{32}H_{32}N_{10}S$=588.

V-TBT: Using 4,7-bis(5-bromo-2-thienyl)-2,1,3-benzothiadiazole (137 mg, 0.30 mmol), 1-hexylvinazene (171 mg, 0.75 mmol), Cy$_2$NMe (0.161 mL, 0.75 mmol), Pd[P(t-Bu)$_3$]$_2$ (3.1 mg, 0.006 mmol), and DMF (2 mL). After workup, the product was obtained as dark red solids (179 mg, 79% yield). $^1$H NMR (CDCl$_3$): δ 0.93 (t, 6H, J=6.8 Hz), 1.39 (unresolved m, 12H), 1.88 (q, 4H, J=6.8 Hz), 4.19 (t, 4H, J=7.2 Hz), 6.64 (d, 2H, J=15.6 Hz), 7.37 (d, 2H, J=4.0 Hz), 7.96 (s, 2H), 8.01 (d, 2H, J=15.2 Hz), 8.09 (d, 2H, J=4.0 Hz). $^{13}$C NMR (C$_4$D$_8$O): δ 14.4, 23.5, 27.1, 31.6, 32.3, 47.2, 109.7, 111.5, 112.9, 13.5, 23.5, 126.9, 129.7, 132.3, 132.9, 142.2, 143.4, 151.0, 153.6. Anal. Calcd for $C_{40}H_{36}N_{10}S_3$: C, 63.80; H, 4.82; N, 18.60; S, 12.78. Found: C, 63.58; H, 4.61; N, 18.57; S, 12.72. MALDI-TOF-MS (dithranol) m/z: 752 (M); calcd. for $C_{40}H_{36}N_{10}S_3$=752.

V-F: Using 2,7-dibromo-9,9'-dimethylfluorene (106 mg, 0.30 mmol), 1-hexylvinazene (171 mg, 0.75 mmol), Cy$_2$NMe (0.161 mL, 0.75 mmol), Pd[P(t-Bu)$_3$]2 (3.1 mg, 0.006 mmol), and DMF (2 mL). After workup, the product was obtained as yellow solids (148 mg, 76% yield). $^1$H NMR (CDCl$_3$): δ 0.91 (t, 6H, J=6.8 Hz), 1.38 (unresolved m, 12H), 1.57 (s, 6H), 1.89 (q, 4H, J=6.8 Hz), 4.21 (t, 4H, J=7.2 Hz), 6.80 (d, 2H, J=15.6 Hz), 7.59 (d, 2H, J=8.4 Hz), 7.59 (overlapping s, 2H), 7.78 (d, 2H, J=7.6 Hz), 7.95 (d, 2H, J=15.6 Hz). $^{13}$C NMR (CDCl$_3$): δ 14.0, 22.5, 26.2, 27.2, 30.8, 31.2, 46.7, 47.2, 108.7, 109.8, 112.0, 112.3, 121.2, 122.2, 123.0, 127.2, 134.9, 140.7, 140.9, 150.2, 155.2. nal. Calcd for $C_{41}H_{42}N_8$: C, 76.13; H, 6.54; N, 17.32. Found: C, 76.01; H, 6.90; N, 17.57. MALDI-TOF-MS (dithranol) m/z: 647 (M+H); calcd. for $C_{41}H_{42}N_8$=46.

Device preparation and characterization: For device fabrication, an approximately 40 nm thick layer of poly(ethylene dioxythiophene) doped with polystyrene sulfonic acid (PEDOT:PSS) was spin-coated onto commercial glass substrates covered with indium-tin-oxide (140 nm). The PEDOT:PSS films were dried on a hot plate under a nitrogen atmosphere for 30 min at 120° C. Next, the photoactive layer of the presented device was spin coated from a 1:1 by weight solution at 2000 RPM and annealed at 140° C. for 10 min. The devices were completed by evaporating a 30 nm Ca layer protected by 100 nm of Ag at a base pressure of 2×10$^{-6}$ mbar. The effective solar cell area as defined by the geometrical overlap between the bottom ITO electrode and the top cathode was 0.14 cm$^2$. All device preparation and characterization were performed under nitrogen atmosphere. To characterize the solar cells the incident-photon-to-current-efficiency (IPCE) was measured. The IPCE is a measure of the external quantum efficiency and is defined as:

$$IPCE = \frac{\text{no. of electrons}}{\text{no. of photons}} = \frac{hcI_{SC}}{c\lambda P_{light}}$$

where 1 is the incident wavelength, $I_{SC}$ is the short-circuit current, e is the elementary charge, h is the Planck constant, c is the speed of light, and Plight the incident light power. The IPCE as a function of wavelength was measured with a home built setup consisting of an Oriel 300 Watt Xe-lamp in combination with an Oriel Cornerstone 130 monochromator and a SRS 830 Lock In amplifier. The number of photons incident on the device was calculated for each wavelength by using a calibrated Si-diode as reference. The white light measurements were performed using a Steuernagel 535 solar cell simulator (1000 W/m2) and a Keithley 2400 Source/Measure unit.

Results

Figures 3, 4:
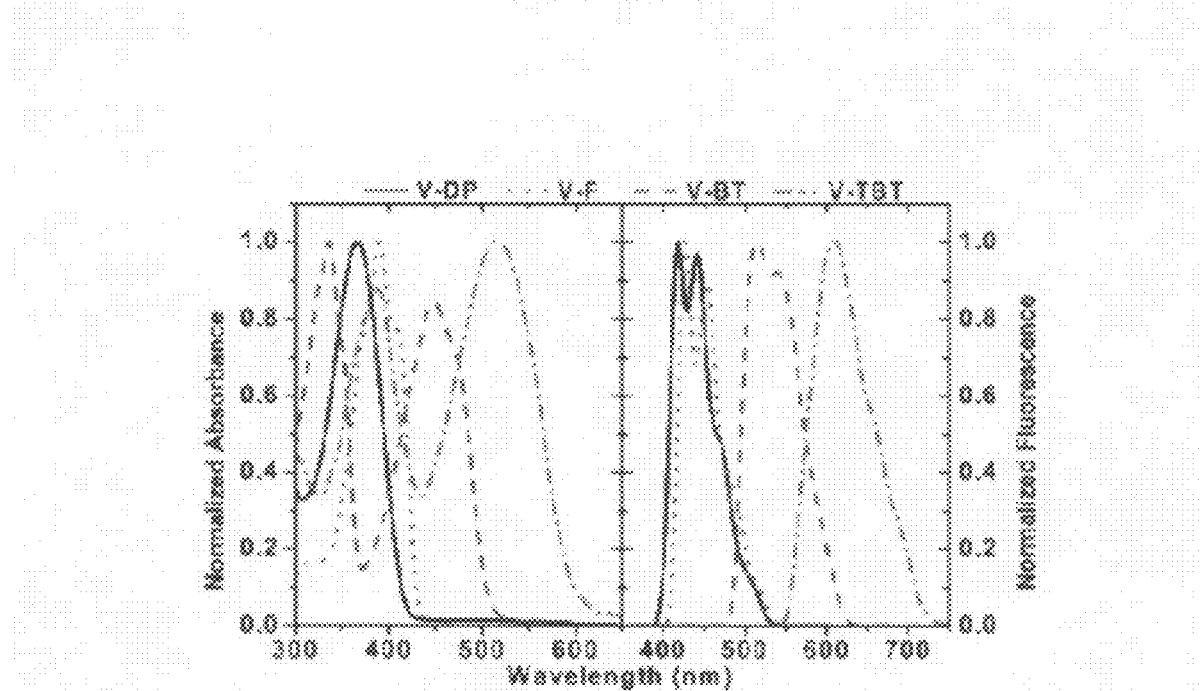
FIG. 3 is a table of physical properties of compounds V-DP, V-F, V-BT and V-TBT.
FIG. 4 is UV-vis and fluorescence spectra of compounds V-DP, V-F, V-BT and V-TBT.

The thermal properties of the materials have been analysed by DSC and TGA and the results are presented in the table shown in FIG. 3. All the materials melt above 205° C. and have relatively high thermal stability (>380° C.) under $N_2$.

The photophysical properties of the compounds were measured by UV-vis and fluorescence spectroscopy in toluene. The compounds show strong absorption and emission in the 330-520 and 410-610 nm (FIG. 4) ranges, respectively. Furthermore, the molecules exhibit high photoluminescence (PL) quantum efficiencies and emission from blue to red, as shown in FIG. 3 and FIG. 4.

Cyclic voltammetry (CV) and the UV-vis absorption band edge were used to estimate the ionization potential (HOMO), electron affinity (LUMO), and band gap of the vinazene materials (Kulkarni et al., *Chem. Mater.* 2004, 16, 4556; D'Andrade et al., *Org. Electron.* 2005, 6, 11; and see FIGS. 7-10). From these results, we observed that the HOMO-LUMO and band gap values could be systematically tuned by changing the central aromatic group as shown in FIG. 3. For example, values ranging from –5.24 to –5.87 eV (HOMO) and –2.84 to –3.49 eV (LUMO) could be obtained using this strategy.

V-BT has very promising properties for solar-cell applications. Its LUMO level is sufficiently low to provide an efficient charge transfer of the photogenerated electron from the donor polymer, such as polyphenylenevinylene (PPV) derivatives or thiophene polymers, to V-BT.

For the solar-cell devices, the following structures were fabricated: glass/ITO/PEDOT:PSS (40 nm)/active layer (70 nm)/Ca (30 nm)/Ag (100 nm), where PEDOT:PSS is 2.5% poly(ethylenedioxythiophene)-polystyrene sulfonic acid in water, and the photoactive layer is 5.0 mg/mL V-BT and 5.0 mg/mL regioregular poly(3-exylthiophene-2,5-diyl) (P3HT) in chloroform. The PEDOT:PSS and photoactive layer were spincoated under a nitrogen atmosphere, whereas the Ca and Ag were thermally sublimed. We found that annealing the photoactive layer at 140° C. for 10 min prior to cathode deposition provided the optimum device efficiencies.

Figure 5:
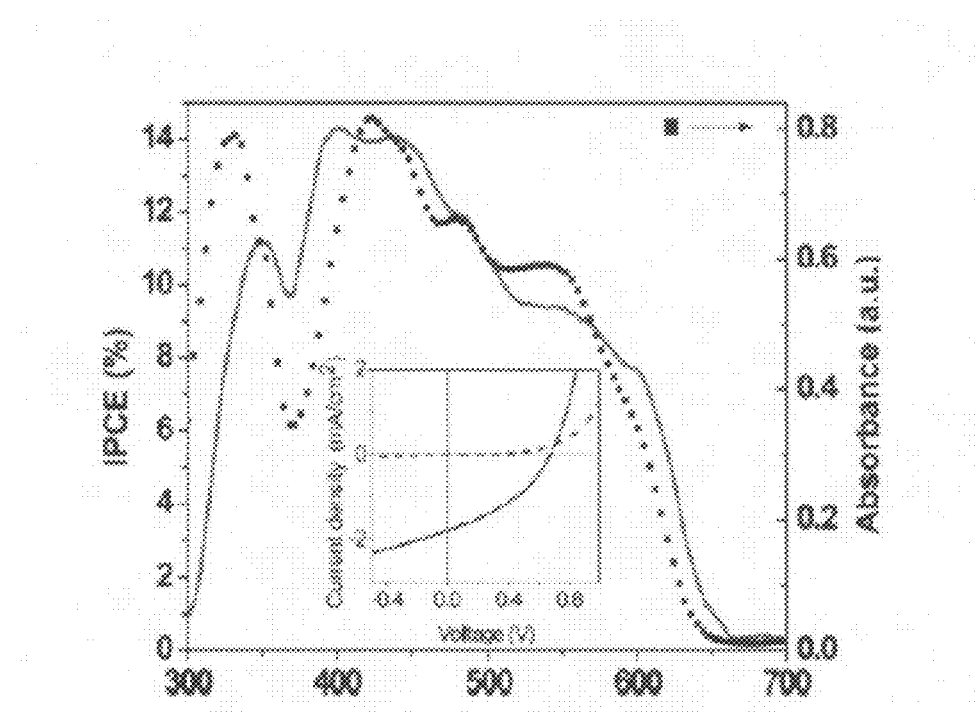
FIG. 5 is IPCE spectra for V-BT:P3HT (1:1) devices annealed at 140° C. for 10 min prior the cathode evaporation. For comparison, the absorbance spectrum of a 1:1 blend is shown. The inset shows the I(V) characteristics under illumination with AM 1.5 irradiation (1000 W/m2, solid line) and under dark conditions (dashed line)

The solar-cell devices demonstrated very good photoresponses in the range from 300 to 650 nm, as shown in FIG. 5, reaching external quantum efficiencies exceeding 14% for 1:1 ratios of V-BT:P3HT. Other ratio variations provided lower efficiencies. The photoresponse resembles the absorbance of the photoactive layer, demonstrating that both materials contribute equally to the photocurrent.

Under white light illumination with a solar simulator (AM 1.5, 1000 W/m$^2$), an open circuit voltage of $V_{oc}$=0.67 V was achieved with a corresponding fill factor and power conversion efficiency of 37% and η=0.45%, respectively.

Figure 6:
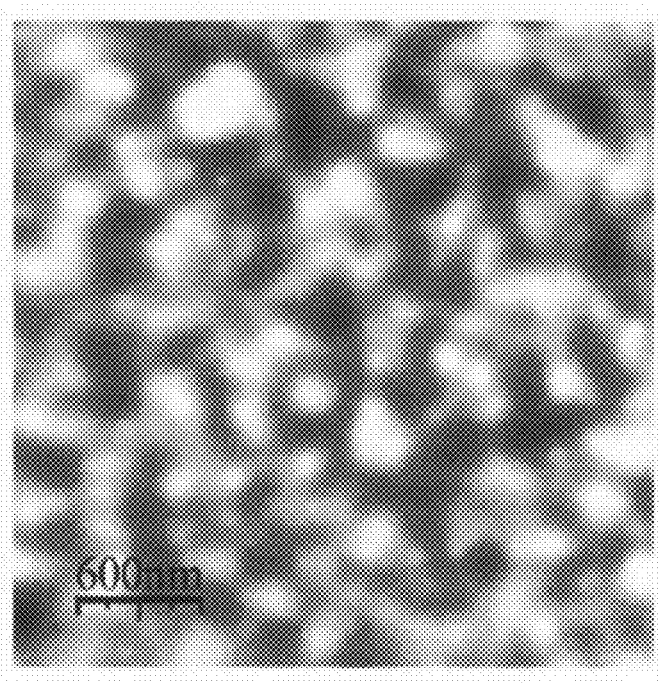
FIG. 6 is an atomic force microscopy (AFM) image of the V-BT:P3HT (1:1) blend layer annealed at 10° C. obtained in tapping mode.
Figure 7:
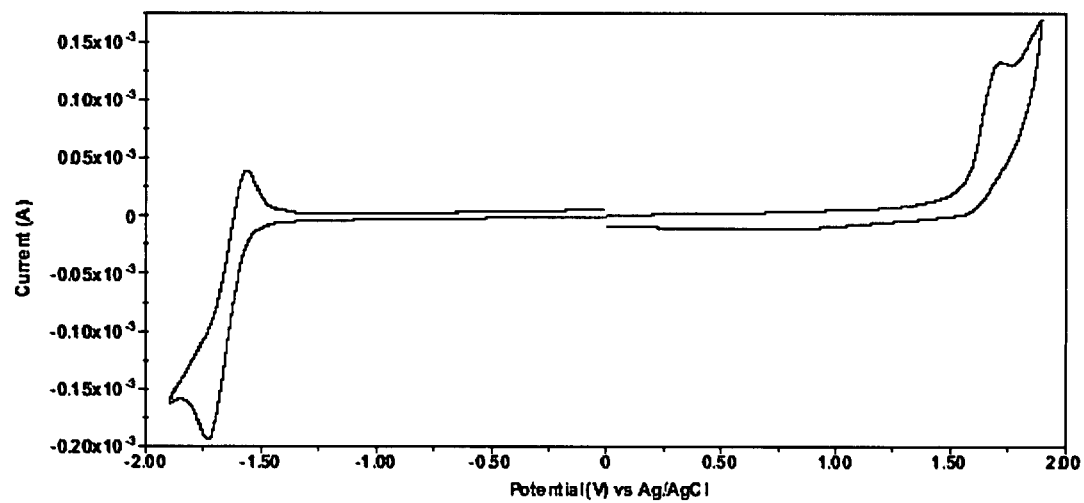
FIG. 7 is a cyclic voltammogram of V-DP.
Figure 8:
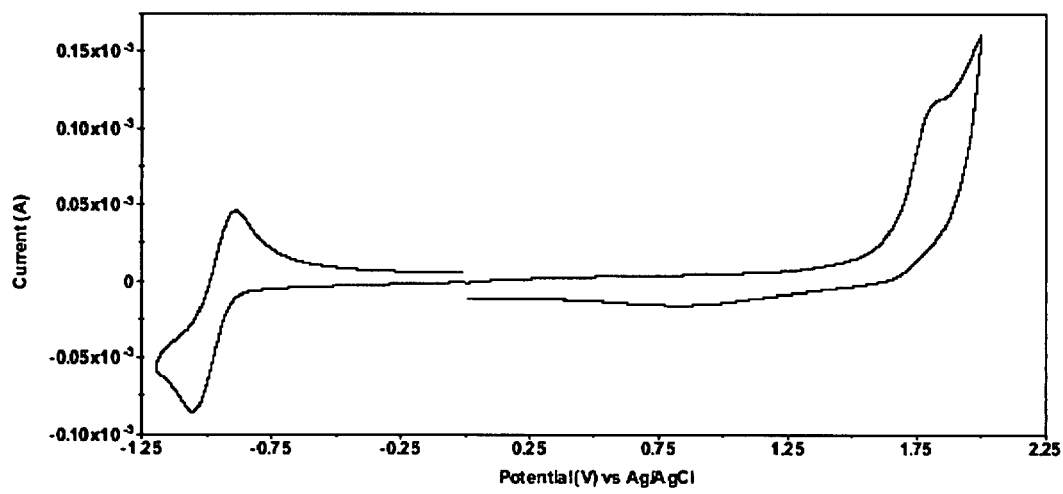
FIG. 8 is a cyclic voltammogram of V-BT.
Figure 9:
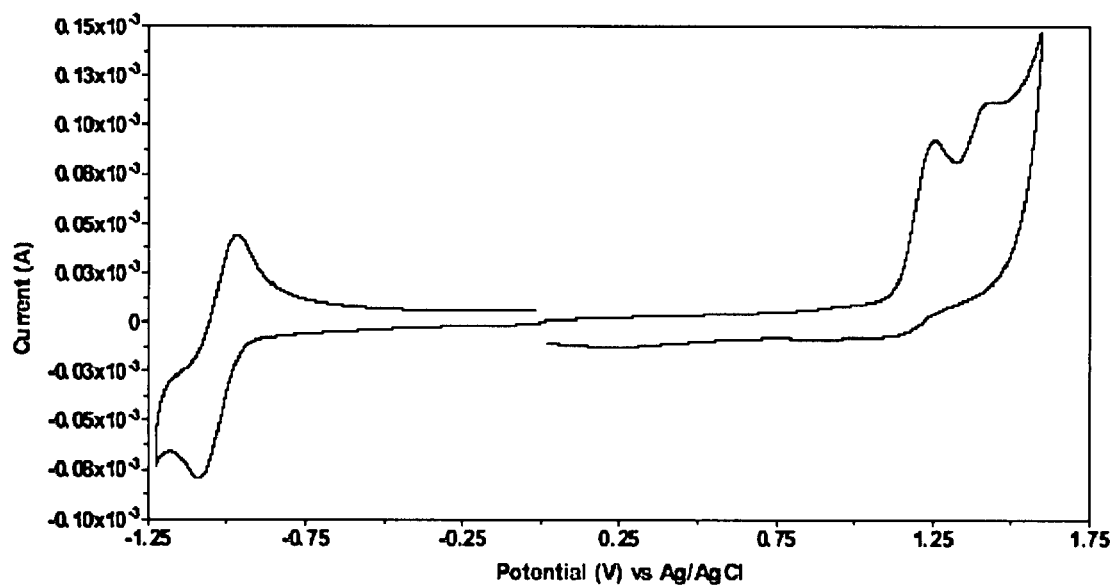
FIG. 9 is a cyclic voltammogram of V-TBT.
Figure 10:
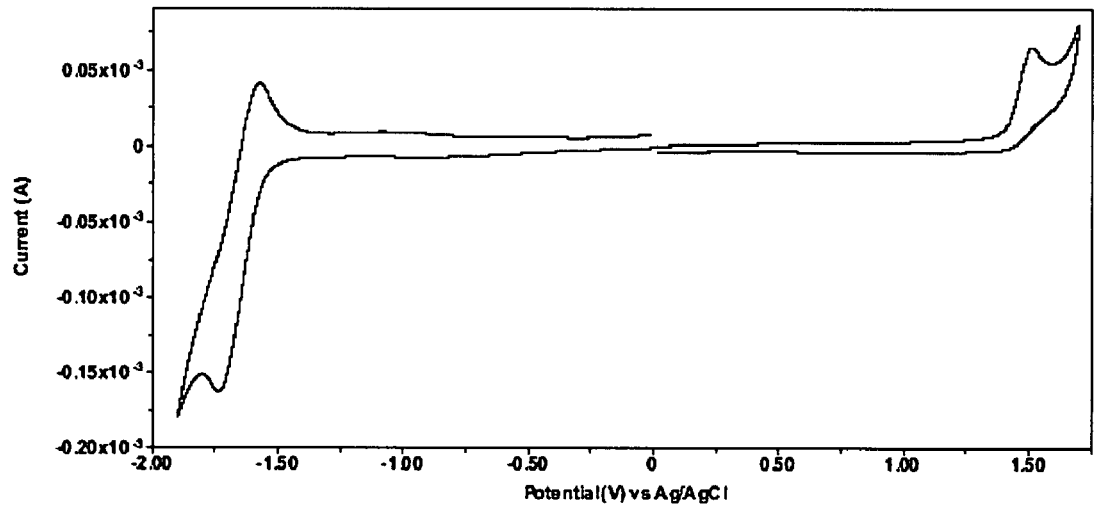
FIG. 10 is a cyclic voltammogram of V-F.

Images from atomic force microscopy (AFM) reveal the photoactive layers having a phase-separated morphology with feature sizes around 100 nm in diameter (FIG. 6), even after annealing at temperatures well below the glass transition of P3HT ($T_{g,P3HT}$=120° C.). Annealing at temperatures higher than 120° C. initially showed an optimum device power efficiency at 140° C. (η=0.45%). However, further annealing at 160° C. led to a power efficiency decrease with an associated increase in phase-separated feature sizes (~1 μm). Because the exciton diffusion length in polymers is estimated to be only about 5-10 nm, most likely not all photogenerated excitons reach the heterointerface and hence limit the device efficiency.

Example 2

Figure 11:
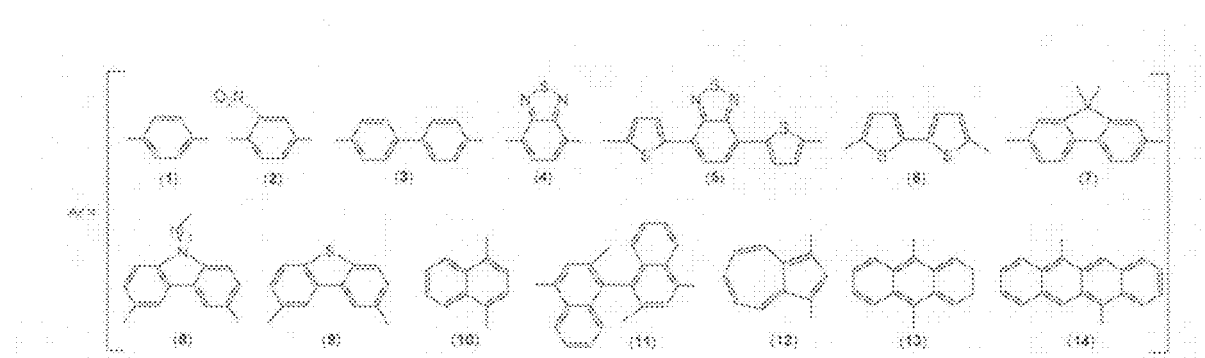
FIG. 11 is a schematic diagram indicating the Ar groups in compounds 1 to 14.
Figure 12:
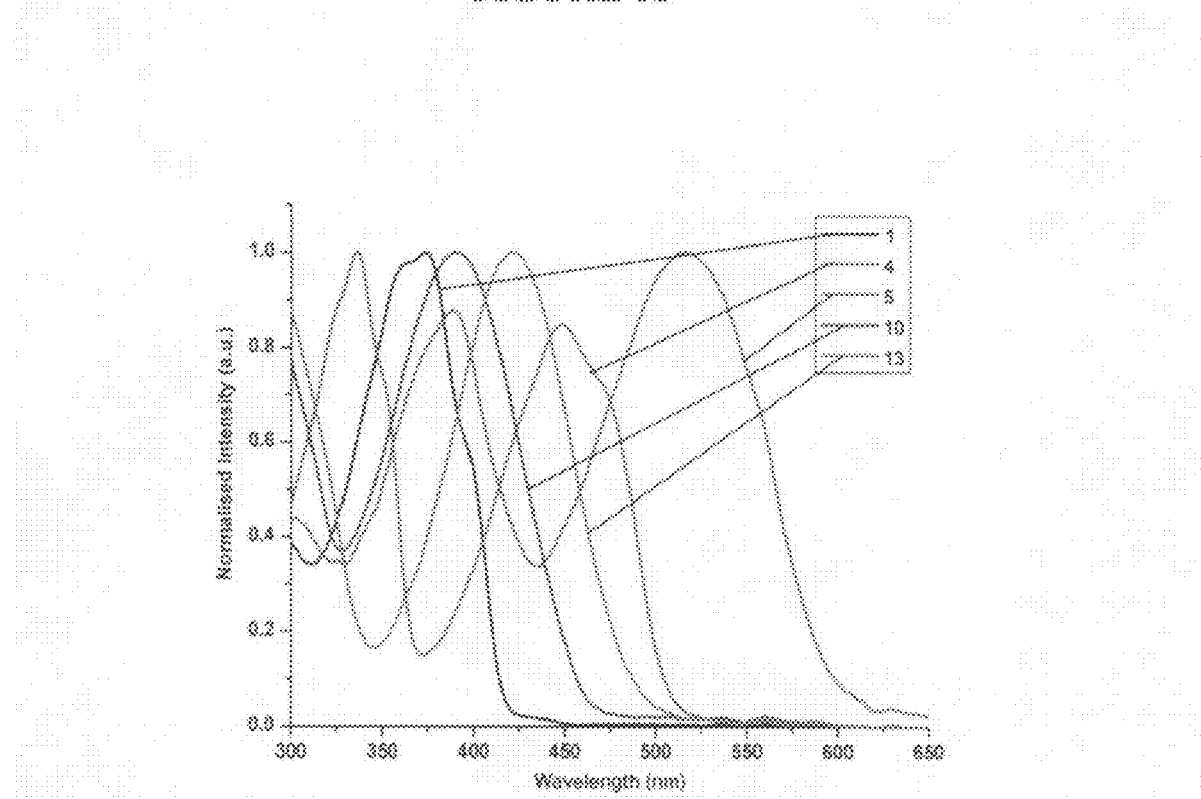
FIG. 12 is UV-vis spectra of compounds 1, 4, 5, 10, 13.

The above-described reactions were carried out using vinazene materials synthesized using the Ar groups indicated in FIG. 11. Compounds 3, 4, 5 and 7 correspond to V-DP, B-BT, B-TBT and V-F, described above.

Details for the Heck Reactions for compounds 1 to 14 are as follows.

1. Using 1,4-dibromobenzene (71 mg, 0.30 mmol), 1-hexylvinazene (171 mg, 0.75 mmol), Cy$_2$NMe (0.161 mL, 0.75 mmol), Pd[P(t-Bu)$_3$]$_2$ (3.1 mg, 0.006 mmol), and DMF (2 mL). After workup, the product was obtained as yellow solids (120 mg, 75% yield). $^1$H NMR (CDCl$_3$): δ 0.90 (t, 6H, J=7.2 Hz), 1.36 (unresolved m, 12H), 1.86 (q, 4H, J=6.8 Hz), 4.19 (t, 4H, J=7.6 Hz), 6.80 (d, 2H, J=16.0 Hz), 7.60 (s, 4H), 7.87 (d, 2H, J=15.6 Hz). $^{13}$C NMR (CDCl$_3$): δ 14.0, 22.5, 26.2, 30.8, 31.2, 46.7, 108.6, 111.2, 111.8, 112.5, 123.0, 128.4, 136.6, 139.5, 149.7. Anal. Calcd for C$_{32}$H$_{34}$N$_8$: C, 72.43; H, 6.46; N, 21.12. Found: C, 72.27; H, 6.79; N, 21.29. MS (MALDI-TOF) m/z 531.37 (M$^+$); calcd. for C$_{32}$H$_{34}$N$_8$=531.29.

2. Using 1,4-dibromo-2-nitrobenzene (84 mg, 0.30 mmol), 1-hexylvinazene (171 mg, 0.75 mmol), Cy$_2$NMe (0.161 mL, 0.75 mmol), Pd[P(t-Bu)$_3$]$_2$ (3.1 mg, 0.006 mmol), and DMF (2 mL). After workup, the product was obtained as yellow solids (138 mg, 80% yield). $^1$H NMR (CDCl$_3$): δ 0.90 (unresolved m, 6H), 1.36 (unresolved m, 12H), 1.88 (unresolved m, 4H), 4.20 and 4.23 (overlapping t, 2H each, J=7.2 Hz), 6.76 (d, 1H, J=15.6 Hz), 6.90 (d, 1H, J=15.6 Hz), 7.72 (d, 1H, J=8.0 Hz), 7.77 (d, 1H, J=8.4 Hz), 7.90 (d, 1H, J=15.6 Hz), 8.22 (d, 1H, J=15.6 Hz), 8.26 (s, 1H). $^{13}$C NMR (C$_4$D$_8$O): δ 14.4, 23.5, 27.1, 31.7, 32.3, 47.3, 47.5, 109.5, 112.7, 112.8, 113.9, 114.0, 115.6, 117.4, 123.5, 130.0, 131.8, 133.4, 134.1, 137.2, 138.9, 150.2, 150.5, 150.8. Anal. Calcd for C$_{32}$H$_{33}$N$_9$O$_2$: C, 66.77; H, 5.78; N, 21.90. Found: C, 67.28; H, 6.08; N, 21.91. MS (MALDI-TOF) m/z 576.36 (M$^+$); calcd. for C$_{32}$H$_{33}$N$_9$O$_2$=576.29.

3 (V-DP). Using 4,4'-dibromobiphenyl (125 mg, 0.40 mmol), 1-ethylhexylvinazene (256 mg, 1.0 mmol), Cy$_2$NMe (0.214 mL, 1.0 mmol), Pd[P(t-Bu)$_3$]$_2$ (4.1 mg, 0.008 mmol), and DMF (2 mL). After workup, the product was obtained as yellow solids (108 mg, 41% yield). $^1$H NMR (CDCl$_3$): δ 0.91 (t, 6H, J=6.0 Hz), 0.98 (t, 6H, J=7.2 Hz), 1.32-1.46 (m, 16H), 1.86 (unresolved m, 2H), 4.07 (d, 4H, J=7.2 Hz), 6.81 (d, 2H, J=15.6 Hz), 7.63 (d, 4H, J=8.0 Hz), 7.69 (d, 4H, J=8.0 Hz), 7.90 (d, 2H, J=15.6 Hz). $^{13}$C NMR (CDCl$_3$): δ 10.8, 14.1, 23.0, 23.9, 28.6, 30.4, 41.2, 50.5, 108.8, 110.5, 112.0, 112.8, 122.8, 127.7, 128.3, 134.5, 139.7, 141.7, 150.3. Anal. Calcd for C$_{42}$H$_{46}$N$_8$: C, 76.10; H, 6.99; N, 16.90. Found: C, 76.04; H, 6.82; N, 16.99. MALDI-TOF-MS (dithranol) m/z: 663 (M+H); calcd. for C$_{42}$H$_{46}$N$_8$=662.

4 (V-BT). Using 4,7-dibromo-2,1,3-benzothiadiazole (88 mg, 0.30 mmol), 1-hexylvinazene (171 mg, 0.75 mmol), Cy$_2$NMe (0.161 mL, 0.75 mmol), Pd[P(t-Bu)3]2 (3.1 mg, 0.006 mmol), and DMF (2 mL). After workup, the product was obtained as an orange solid (155 mg, 88% yield). $^1$H NMR (CDCl$_3$): δ 0.90 (t, 6H, J=7.2 Hz), 1.37 (unresolved m, 12H), 1.95 (q, 4H, J=7.2 Hz), 4.30 (t, 4H, J=7.2 Hz), 7.74 (s, 2H), 8.06 (d, 2H, J=15.6 Hz), 8.33 (d, 2H, J=15.6 Hz). $^{13}$C NMR (CDCl$_3$): δ 14.0, 22.5, 26.2, 30.8, 31.2, 46.9, 108.6, 111.9, 112.7, 117.4, 123.2, 129.4, 132.5, 135.5, 150.2, 153.8. Anal. Calcd for C$_{32}$H$_{32}$N$_{10}$S: C, 65.28; H, 5.48; N, 23.79; S, 5.45. Found: C, 64.75; H, 5.37; N, 24.06; S, 5.19. MALDI-TOF-MS (dithranol) m/z: 589 (M+H); calcd. for C$_{32}$H$_{32}$N$_{10}$S=588.

5 (V-TBT). Using 4,7-bis(5-bromo-2-thienyl)-2,1,3-benzothiadiazole (137 mg, 0.30 mmol), 1-hexylvinazene (171 mg, 0.75 mmol), Cy$_2$NMe (0.161 mL, 0.75 mmol), Pd[P(t-Bu)$_3$]$_2$ (3.1 mg, 0.006 mmol), and DMF (2 mL). After workup, the product was obtained as dark red solids (179 mg, 79% yield). $^1$H NMR (CDCl$_3$): δ 0.93 (t, 6H, J=6.8 Hz), 1.39 (unresolved m, 12H), 1.88 (q, 4H, J=6.8 Hz), 4.19 (t, 4H, J=7.2 Hz), 6.64 (d, 2H, J=15.6 Hz), 7.37 (d, 2H, J=4.0 Hz), 7.96 (s, 2H), 8.01 (d, 2H, J=15.2 Hz), 8.09 (d, 2H, J=4.0 Hz). $^{13}$C NMR (C$_4$D$_8$O): δ 14.4, 23.5, 27.1, 31.6, 32.3, 47.2, 109.7, 111.5, 112.9, 13.5, 23.5, 126.9, 129.7, 132.3, 132.9, 142.2, 143.4, 151.0, 153.6. Anal. Calcd for C$_{40}$H$_{36}$N$_{10}$S$_3$: C, 63.80; H, 4.82; N, 18.60; S, 12.78. Found: C, 63.58; H, 4.61; N, 18.57; S, 12.72. MALDI-TOF-MS (dithranol) m/z: 752 (M); calcd. for C$_{40}$H$_{36}$N$_{10}$S$_3$=752.

6. Using 5,5'-dibromo-2,2'-bithiophene (130 mg, 0.40 mmol), 1-ethylhexylvinazene (256 mg, 1.0 mmol), Cy$_2$NMe (0.214 mL, 1.0 mmol), Pd[P(t-Bu)$_3$]$_2$ (4.1 mg, 0.008 mmol), and DMF (2 mL). After workup, the product was obtained as red solids (125 mg, 46% yield). $^1$H NMR (CDCl$_3$): δ 0.93 (t, 6H, J=7.2 Hz), 0.98 (t, 6H, J=7.6 Hz), 1.35 (unresolved m, 16H), 1.83 (unresolved m, 2H), 4.02 (unresolved m, 4H), 6.49 (d, 2H, J=15.6 Hz), 7.19 (s, 4H), 7.89 (d, 2H, J=15.2 Hz). $^{13}$C NMR (CDCl$_3$): δ 10.8, 14.1, 23.0, 24.0, 28.6, 30.5, 41.2, 50.4, 108.8, 109.6, 111.9, 112.8, 122.9, 125.8, 132.0, 132.3, 138.8, 140.0, 149.9. Anal. Calcd for C$_{38}$H$_{42}$N$_8$S$_2$: C, 67.62; H, 6.27; N, 16.60; S, 9.50. Found: C, 67.85; H, 6.44; N, 16.46; S, 9.74. MS (MALDI-TOF) m/z 674.36 (M$^+$). calcd. for C$_{38}$H$_{42}$N$_8$S$_2$=674.30.

7 (V-F). Using 2,7-dibromo-9,9'-dimethylfluorene (106 mg, 0.30 mmol), 1-hexylvinazene (171 mg, 0.75 mmol), Cy$_2$NMe (0.161 mL, 0.75 mmol), Pd[P(t-Bu)$_3$]2 (3.1 mg, 0.006 mmol), and DMF (2 mL). After workup, the product was obtained as yellow solids (148 mg, 76% yield). $^1$H NMR (CDCl$_3$): δ 0.91 (t, 6H, J=6.8 Hz), 1.38 (unresolved m, 12H), 1.57 (s, 6H), 1.89 (q, 4H, J=6.8 Hz), 4.21 (t, 4H, J=7.2 Hz), 6.80 (d, 2H, J=15.6 Hz), 7.59 (d, 2H, J=8.4 Hz), 7.59 (overlapping s, 2H), 7.78 (d, 2H, J=7.6 Hz), 7.95 (d, 2H, J=15.6 Hz). $^{13}$C NMR (CDCl$_3$): δ 14.0, 22.5, 26.2, 27.2, 30.8, 31.2, 46.7, 47.2, 108.7, 109.8, 112.0, 112.3, 121.2, 122.2, 123.0, 127.2, 134.9, 140.7, 140.9, 150.2, 155.2. nal. Calcd for C$_{41}$H$_{42}$N$_8$: C, 76.13; H, 6.54; N, 17.32. Found: C, 76.01; H, 6.90; N, 17.57. MALDI-TOF-MS (dithranol) m/z: 647 (M+H); calcd. for C$_{41}$H$_{42}$N$_8$=46.

8. Using N-hexyl-3,6-dibromocarbazole (123 mg, 0.30 mmol), 1-hexylvinazene (171 mg, 0.75 mmol), Cy$_2$NMe (0.161 mL, 0.75 mmol), Pd[P(t-Bu)$_3$]$_2$ (3.1 mg, 0.006 mmol), and DMF (2 mL). After workup, the product was obtained as yellow solids (161 mg, 76% yield). $^1$H NMR (C$_4$D$_8$O): δ 0.88 (t, 3H, J=6.4 Hz), δ 0.92 (t, 6H, J=6.8 Hz), 1.38 (unresolved m, 18H), 1.90 (unresolved m, 6H), 4.35 (t, 4H, J=7.2 Hz), 4.45 (t, 2H, J=6.8 Hz), 7.12 (d, 2H, J=15.6 Hz), 7.59 (d, 2H, J=8.8 Hz), 7.86 (d, 2H, J=8.4 Hz), 8.06 (d, 2H, J=15.6 Hz), 8.43 (s, 2H). $^{13}$C NMR (C$_4$D$_8$O): δ 14.4, 23.5, 23.6, 27.1, 27.9, 30.1, 31.6, 32.3, 32.7, 44.2, 47.1, 109.5, 109.8, 110.8, 113.1, 121.8, 123.4, 124.5, 126.6, 128.5, 141.5, 143.2, 151.9. Anal. Calcd for C$_{44}$H$_{49}$N$_9$: C, 75.08; H, 7.02; N, 17.91. Found: C, 74.87; H, 6.89; N, 17.92. MS (MALDI-TOF) m/z 704.51 (M$^+$); calcd. for C$_{44}$H$_{49}$N$_9$=704.41.

9. Using 3,6-dibromo-dibenzothiophene (103 mg, 0.30 mmol), 1-hexylvinazene (171 mg, 0.75 mmol), Cy$_2$NMe (0.161 mL, 0.75 mmol), Pd[P(t-Bu)$_3$]$_2$ (3.1 mg, 0.006 mmol), and DMF (2 mL). After workup, the product was obtained as yellow solids (166 mg, 87% yield). $^1$H NMR (C$_4$D$_8$O): δ 0.91 (t, 6H, J=6.8 Hz), 1.38 (unresolved m, 12H), 1.91 (q, 4H, J=7.2 Hz), 4.40 (t, 4H, J=6.8 Hz), 7.33 (d, 2H, J=16.0 Hz), 7.92 (d, 2H, J=7.6 Hz), 8.00 (d, 2H, J=8.4 Hz), 8.07 (d, 2H, J=15.6 Hz), 8.59 (s, 2H). $^{13}$C NMR (C$_4$D$_8$O): δ 14.5, 23.5, 27.1, 31.7, 32.4, 47.2, 109.7, 112.3, 113.0, 113.5, 123.1, 123.3, 124.4, 126.7, 133.7, 137.1, 140.1, 142.3, 151.3. Anal. Calcd for C$_{38}$H$_{36}$N$_8$S: C, 71.67; H, 5.70; N, 17.60; S, 5.04. Found: C, 71.57; H, 5.93; N, 17.53; S, 5.04. MS (MALDI-TOF) m/z 637.35 (M$^+$); calcd. for C$_{38}$H$_{36}$N$_8$S=637.28.

10. Using 1,4-dibromonaphthalene (86 mg, 0.30 mmol), 1-hexylvinazene (171 mg, 0.75 mmol), Cy$_2$NMe (0.161 mL, 0.75 mmol), Pd[P(t-Bu)$_3$]$_2$ (3.1 mg, 0.006 mmol), and DMF (2 mL). After workup, the product was obtained as orange solids (138 mg, 79% yield). $^1$H NMR (CDCl$_3$): δ 0.89 (t, 6H, J=6.8 Hz), 1.34 (unresolved m, 12H), 1.87 (q, 4H, J=7.2 Hz), 4.20 (t, 4H, J=7.2 Hz), 6.88 (d, 2H, J=15.2 Hz), 7.67-7.70 (m, 2H), 7.78 (s, 2H), 8.28-8.30 (m, 2H), 8.68 (d, 2H, J=15.6 Hz). $^{13}$C NMR (CDCl$_3$): δ 14.0, 22.5, 26.2, 30.9, 31.2, 46.8, 108.6, 111.9, 112.5, 113.7, 122.9, 124.0, 124.4, 127.7, 131.7, 134.7, 137.2, 149.7. Anal. Calcd for C$_{36}$H$_{36}$N$_8$: C, 74.46; H, 6.25; N, 19.30. Found: C, 74.07; H, 6.28; N, 19.24. MS (MALDI-TOF) m/z 581.46 (M$^+$); calcd. for C$_{36}$H$_{36}$N$_8$=581.31.

11. Using 4,4'-dibromo-2,2'-dimethyl-1,1'-binaphthalyl (133 mg, 0.30 mmol), 1-hexylvinazene (171 mg, 0.75 mmol), Cy$_2$NMe (0.161 mL, 0.75 mmol), Pd[P(t-Bu)$_3$]$_2$ (3.1 mg, 0.006 mmol), and DMF (2 mL). After workup, the product was obtained as yellow solids (121 mg, 55% yield). $^1$H NMR (CDCl$_3$): δ 0.91 (t, 6H, J=6.8 Hz), 1.38 (unresolved m, 12H), 1.93 (q, 4H, J=7.2 Hz), 2.11 (s, 6H), 4.27 (t, 4H, J=7.2 Hz), 6.95 (d, 2H, J=15.6 Hz), 7.12 (d, 2H, J=8.4 Hz), 7.30 (t, 2H, J=7.6 Hz), 7.53 (t, 2H, J=7.6 Hz), 7.79 (s, 2H), 8.30 (d, 2H, J=8.8 Hz), 8.78 (d, 2H, J=15.2 Hz). $^{13}$C NMR (CDCl$_3$): δ 14.0, 20.3, 22.5, 26.3, 30.9, 31.3, 46.8, 108.7, 112.0, 112.4, 112.9, 122.9, 123.8, 126.4, 127.1, 127.2, 130.4, 132.4, 133.1, 134.1, 137.3, 137.9, 150.1. Anal. Calcd for C$_{48}$H$_{46}$N$_8$: C, 78.44; H, 6.31; N, 15.25. Found: C, 77.51; H, 6.38; N, 15.11. MS (MALDI-TOF) m/z 735.53 (M$^+$); calcd. for C$_{48}$H$_{46}$N$_8$=735.39.

12. Using 1,3-dibromoazulene (86 mg, 0.30 mmol), 1-hexylvinazene (171 mg, 0.75 mmol), Cy$_2$NMe (0.161 mL, 0.75 mmol), Pd[P(t-Bu)$_3$]$_2$ (3.1 mg, 0.006 mmol), and DMF (2 mL). After workup, the product was obtained as brown solids (131 mg, 75% yield). $^1$H NMR (CDCl$_3$): δ 0.91 (t, 6H, J=7.2 Hz), 1.37 (unresolved m, 12H), 1.91 (q, 4H, J=7.2 Hz), 4.22 (t, 4H, J=7.2 Hz), 6.83 (d, 2H, J=15.6 Hz), 7.44 (t, 2H, J=9.6 Hz), 7.80 (t, 1H, J=9.6 Hz), 8.43 (d, 2H, J=15.6 Hz), 8.47 (s, 1H), 8.64 (d, 2H, J=9.6 Hz). $^{13}$C NMR (CDCl$_3$): δ 14.1, 22.5, 26.2, 30.8, 31.3, 46.5, 108.3, 108.9, 112.0, 112.1, 122.8, 125.6, 127.5, 130.0, 131.2, 135.4, 141.1, 141.6, 150.9. Anal. Calcd for C$_{36}$H$_{36}$N$_8$: C, 74.46; H, 6.25; N, 19.30. Found: C, 73.94; H, 7.09; N, 19.14. MS (MALDI-TOF) m/z 581.41 (M$^+$); calcd. for C$_{36}$H$_{36}$N$_8$=581.31.

13. Using 9,10-dibromoanthracene (101 mg, 0.30 mmol), 1-hexylvinazene (171 mg, 0.75 mmol), Cy$_2$NMe (0.161 mL, 0.75 mmol), Pd[P(t-Bu)$_3$]$_2$ (3.1 mg, 0.006 mmol), and DMF (2 mL). After workup, the product was obtained as yellow solids (146 mg, 77% yield). $^1$H NMR (CDCl$_3$): δ 0.86 (t, 6H, J=6.8 Hz), 1.31 (unresolved m, 12H), 1.84 (q, 4H, J=6.8 Hz), 4.15 (t, 4H, J=7.2 Hz), 6.75 (d, 2H, J=16.0 Hz), 7.55-7.58 (m, 4H), 8.28-8.30 (m, 4H), 8.80 (d, 2H, J=16.0 Hz). $^{13}$C NMR (CD$_2$Cl$_2$): 14.0, 22.8, 26.5, 31.3, 31.6, 47.3, 112.5, 120.7, 126.3, 126.8, 129.7, 132.1, 137.6. Anal. Calcd for C$_{40}$H$_{38}$N$_8$: C, 76.16; H, 6.07; N, 17.76. Found: C, 75.89; H, 6.28; N, 17.50. MS (MALDI-TOF) m/z 631.49 (M$^+$); calcd. for C$_{40}$H$_{38}$N$_8$=631.32.

14. Using 5,11-dibromotetracene (116 mg, 0.30 mmol), 1-hexylvinazene (171 mg, 0.75 mmol), Cy$_2$NMe (0.161 mL, 0.75 mmol), Pd[P(t-Bu)$_3$]$_2$ (3.1 mg, 0.006 mmol), and DMF (2 mL). After workup, the product was obtained as yellow solids (89 mg, 54% yield). $^1$H NMR (CDCl$_3$): δ 0.84 (t, 6H, J=6.8 Hz), 1.30 (unresolved m, 12H), 1.87 (q, 4H, J=7.2 Hz), 4.17 (t, 4H, J=7.2 Hz), 6.87 (d, 2H, J=16.0 Hz), 7.46-7.52 (m, 4H), 8.00-8.05 (m, 2H), 8.26-8.30 (m, 2H), 8.91 (s, 2H), 8.96 (d, 2H, J=16.0 Hz). $^{13}$C NMR (CDCl$_3$): δ 13.9, 22.5, 26.2, 31.1, 31.2, 46.9, 108.6, 111.9, 112.6, 119.9, 120.2, 123.1, 124.6, 125.1, 125.9, 126.0, 126.4, 126.6, 127.2, 128.0, 128.5, 129.1, 129.4, 129.7, 130.6, 131.6, 131.8, 132.0, 137.6, 137.7, 149.5. Anal. Calcd for C$_{44}$H$_{40}$N$_8$: C, 77.62; H, 5.92; N, 16.46. Found: C, 76.05; H, 5.92; N, 16.17. MS (MALDI-TOF) m/z 680.46 (M$^+$); calcd. for C$_{44}$H$_{40}$N$_8$=680.34.

Results of characterization of various of the compounds are shown in FIGS. 12 to 28.

Figure 13:
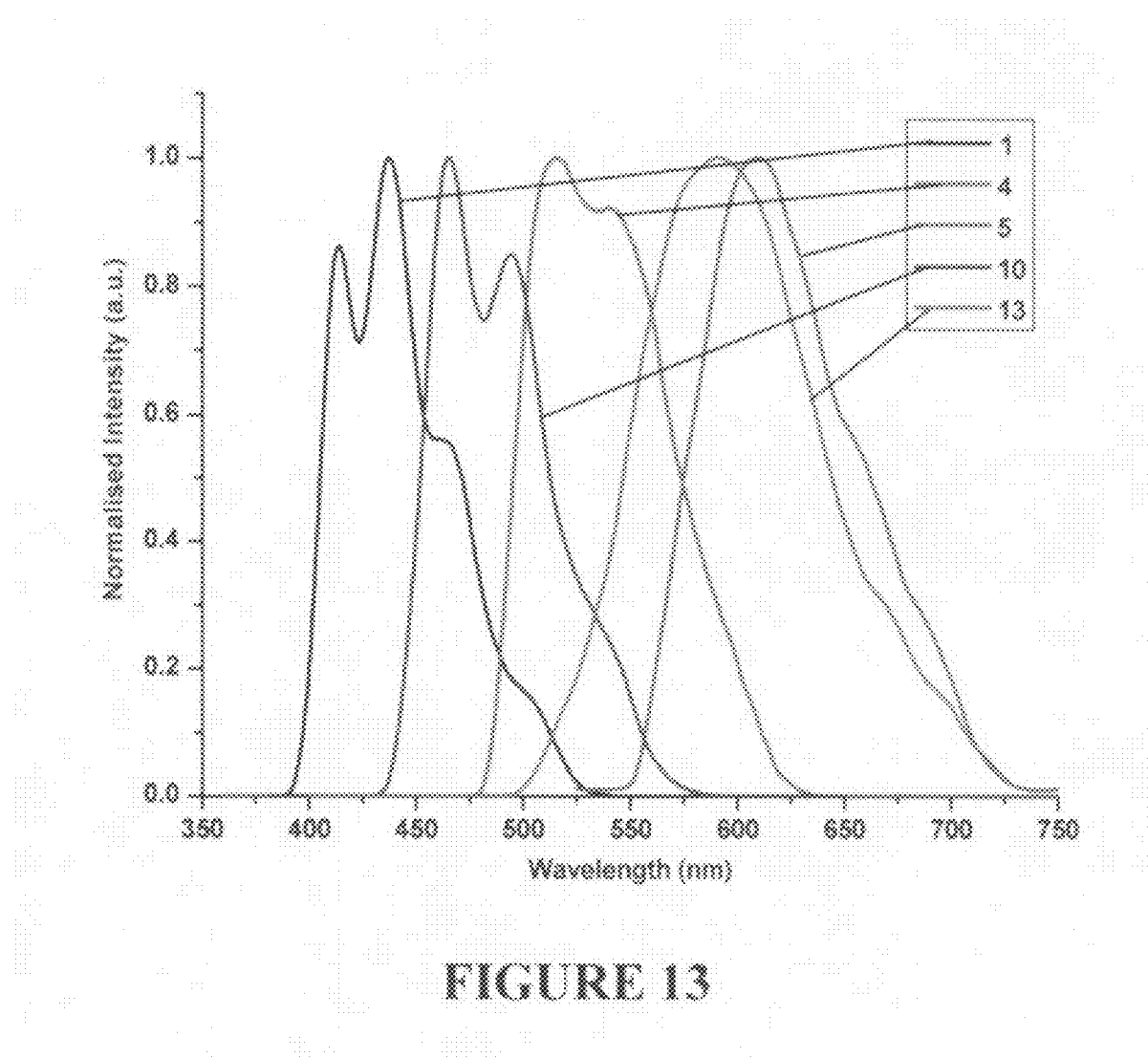
FIG. 13 is photoluminescence spectra of compounds 1, 4, 5, 10, 13.

As seen in FIG. 13, the $\lambda_{max}$ of the photoluminscence spectra could be tuned from 437 to 606 nm by selection of the particular arylene group incorporated into the compounds.

Figure 15:
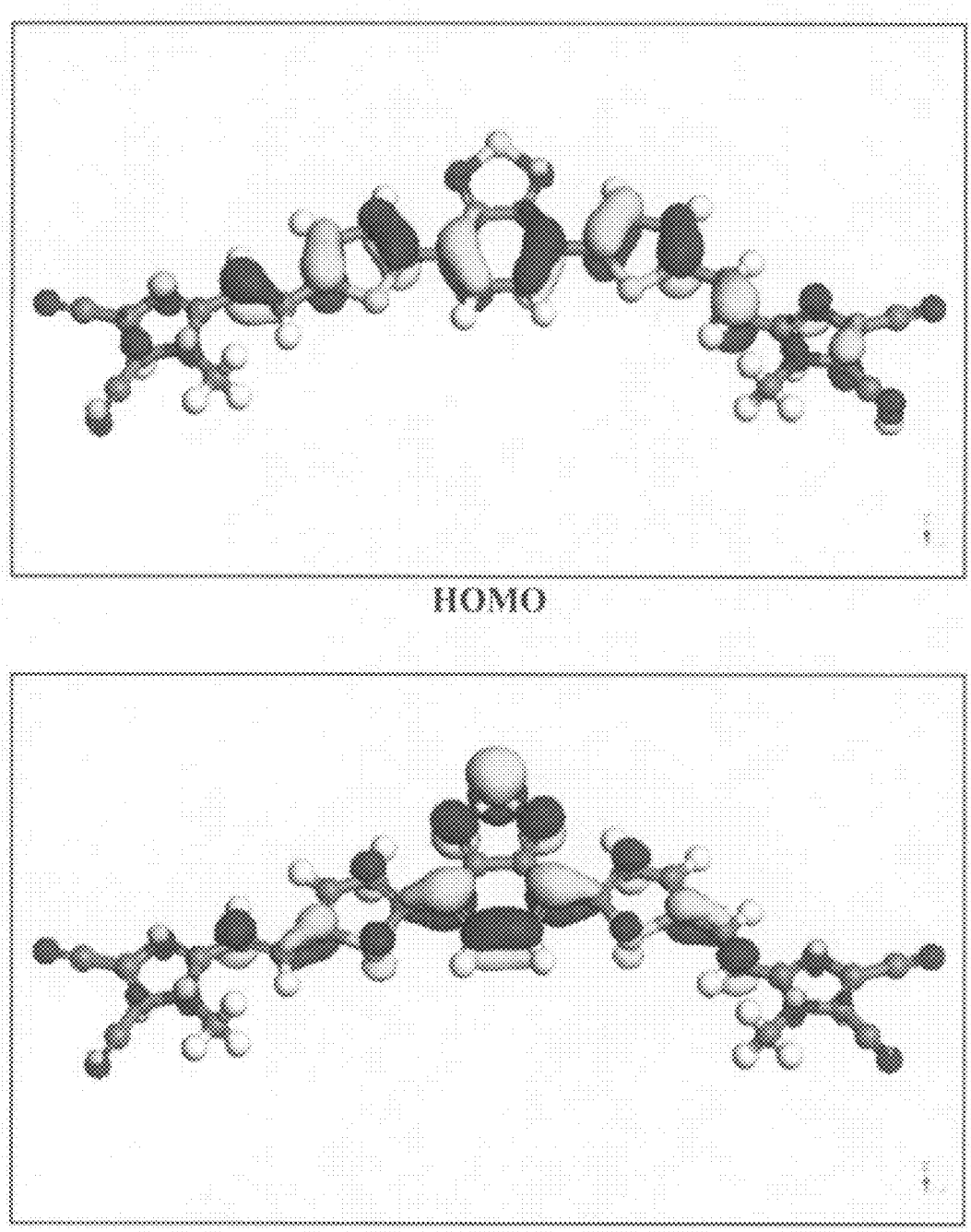
FIG. 15 is a diagram depicting the HOMO and LUMO for compound 4.

The HOMO and LUMO for compound 4 (V-BT) is shown in FIG. 15. The compound showed good electron delocalisation over the whole molecule.

Figure 16:
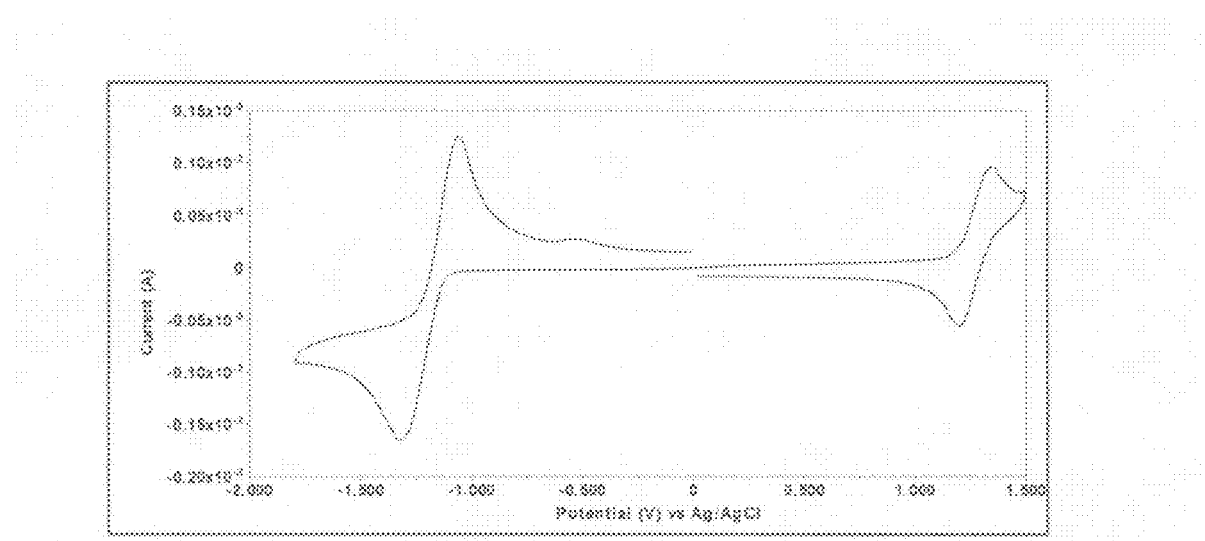
FIG. 16 is a cyclic voltammogram for compound 13.
Figure 17:
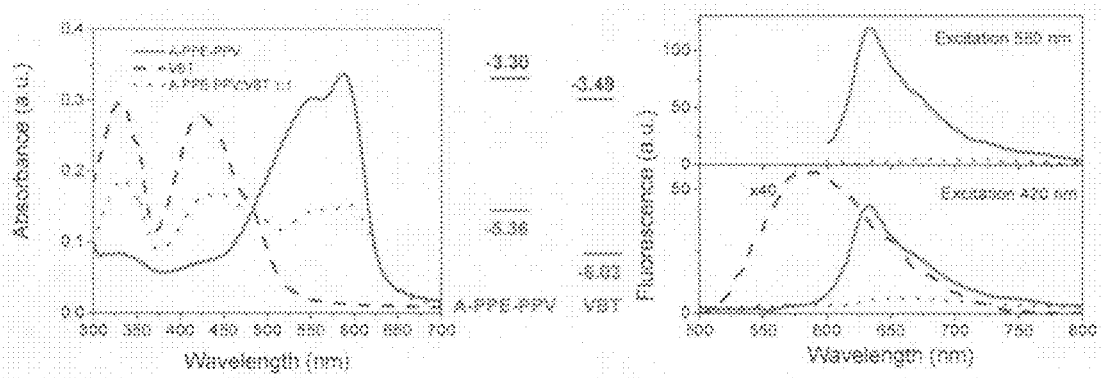
FIG. 17 is absorbance and fluorescence spectra for a photovoltaic cell containing A-PPE-PPV and V-BT, and a diagram of relative HOMO and LUMO energies for the two compounds.

A cyclic voltammogram for compound 13 is shown in FIG. 16. The HOMO and LUMO energy levels were −5.60 and −3.27 eV, with a bandgap of 2.33 eV.

Figure 18:
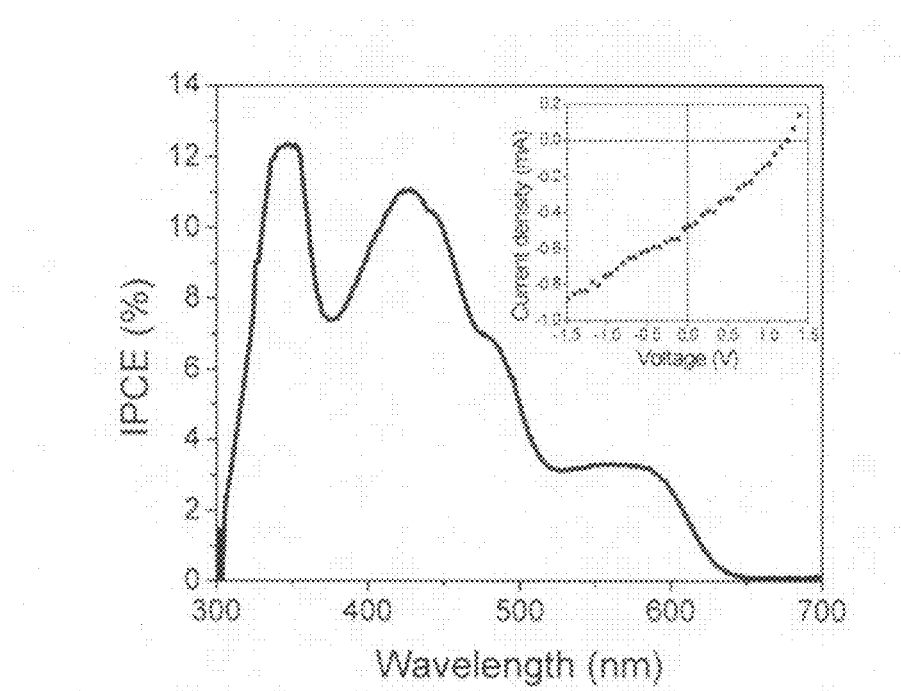
FIG. 18 is an IPCE spectrum for a photovoltaic containing compound 4 as electron acceptor.

The photovoltaic performance of compound 4 is shown in FIG. 18. The incident-photon-to-current-efficiency was 12%, more than half of that for a device containing PCBM:A-PPE-PPV. The V$_{oc}$ measured was 1.23 V, markedly greater than the 0.6 to 0.8 V typically measured for PCBM-based photovoltaic cells.

Figure 19:
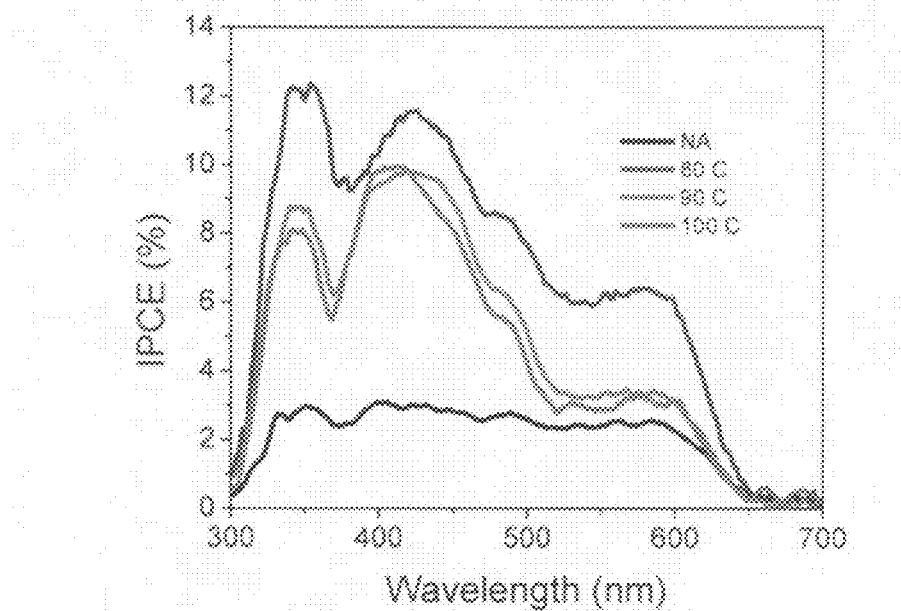
FIG. 19 is IPCE spectra for a photovoltaic containing compound 4 as electron acceptor, at various annealing temperatures.
Figure 20:
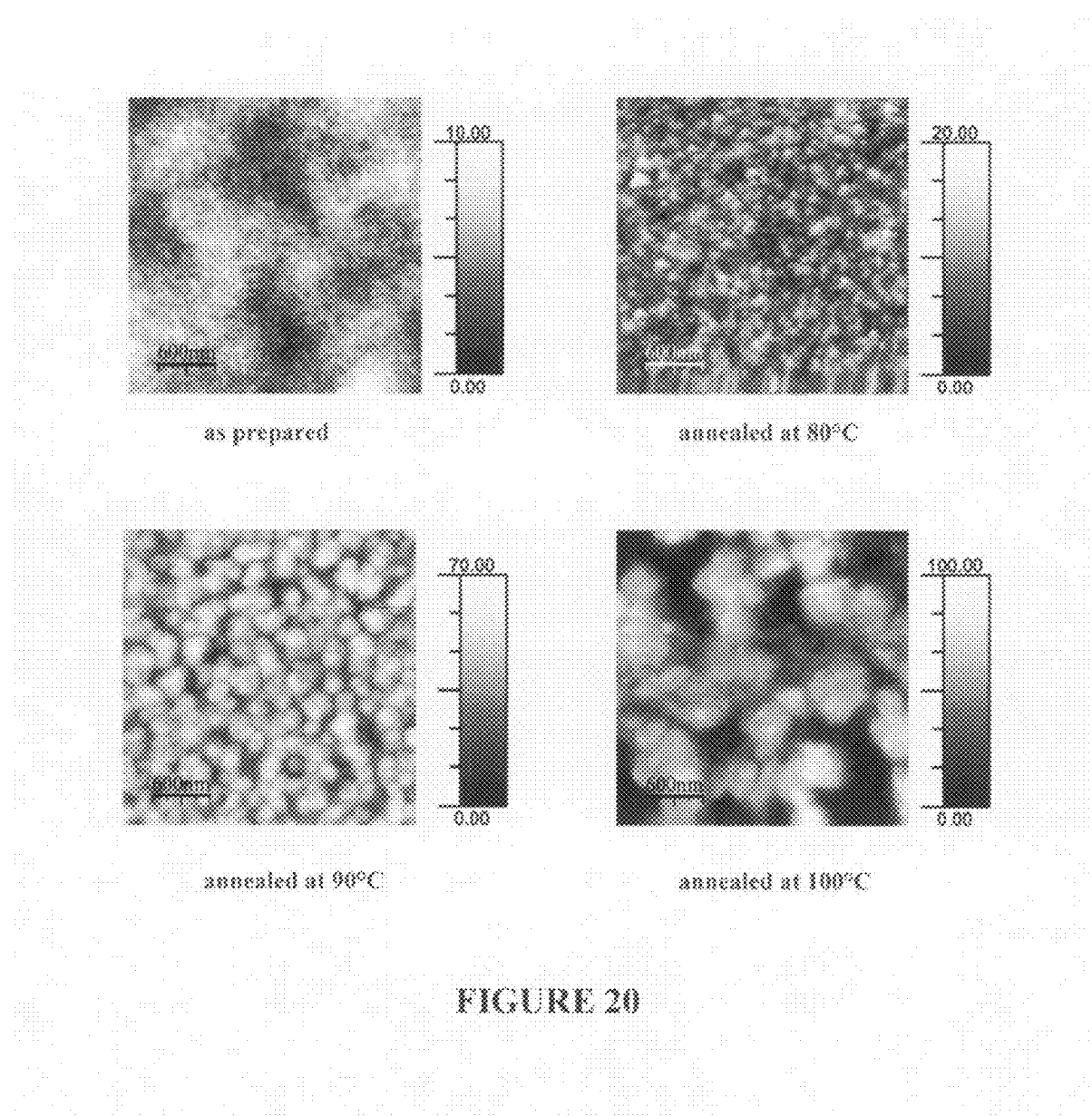
FIG. 20 is atomic force micrographs of layers of compound 4 annealed at various temperatures.
Figure 21:
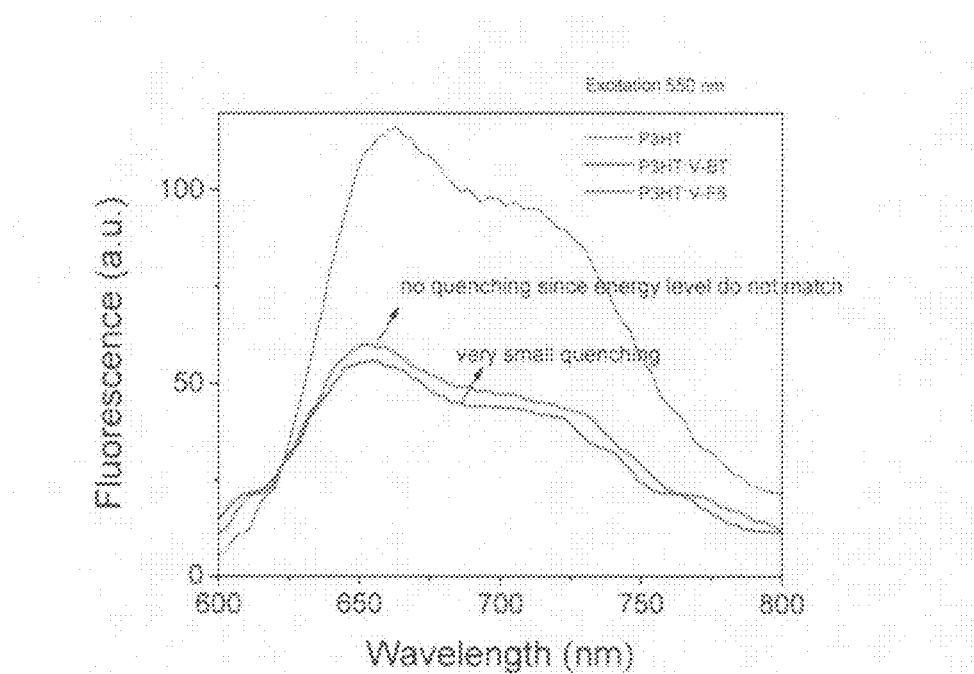
FIG. 21 is fluorescence spectra of P3HT, P3HT:V-BT blend and P3HT:V-F8 blend.
Figure 22:
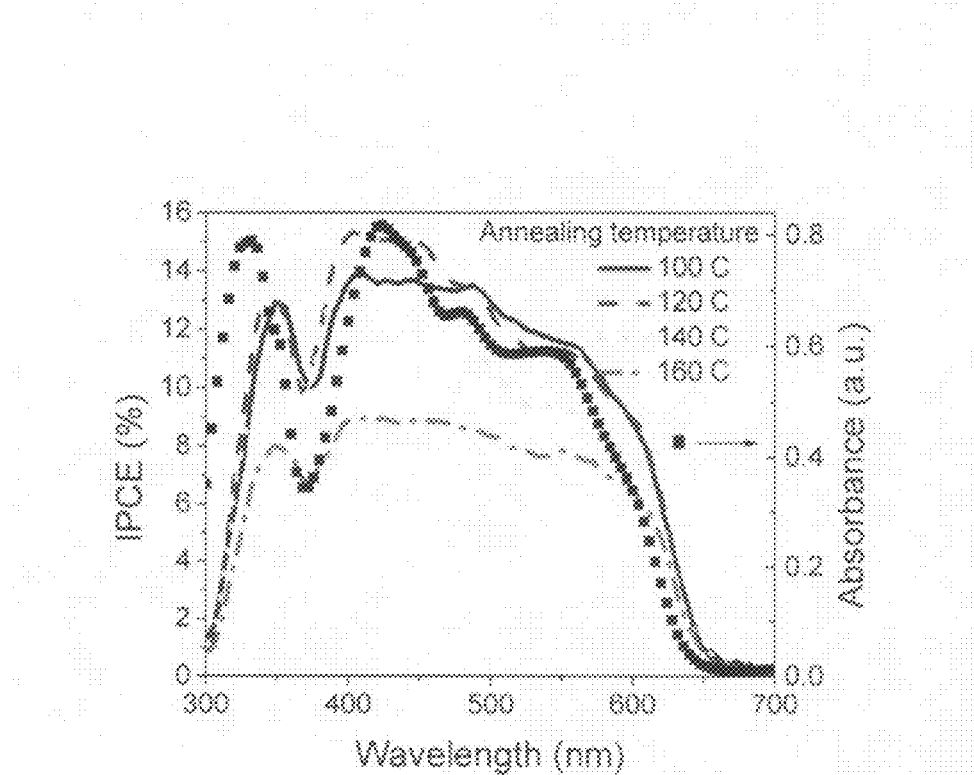
FIG. 22 is IPCE spectra for a device containing P3HT:V-BT blend annealed at various temperatures.

The influence of annealing temperature can be seen in FIG. 19, as measured for compound 4 at 80, 90 and 100° C. (NA=not annealed). The annealing lead to pronounced contribution of compound 4, with the highest energy conversion efficiency observed after annealing at 80° C. for 10 minutes (the ECE=0.42% at annealing temperature of 80° C.).

Figure 23:
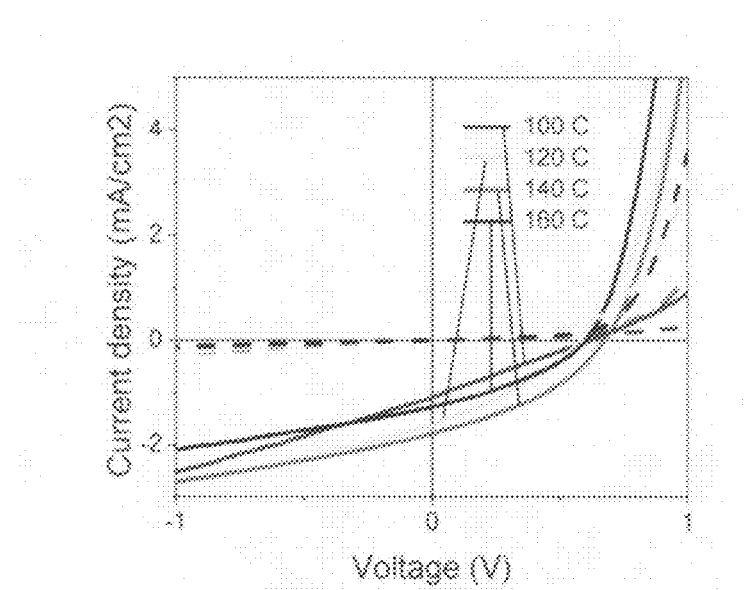
FIG. 23 is an I(V) graph for devices containing P3HT:V-BT blend annealed at various temperatures.
Figure 24:
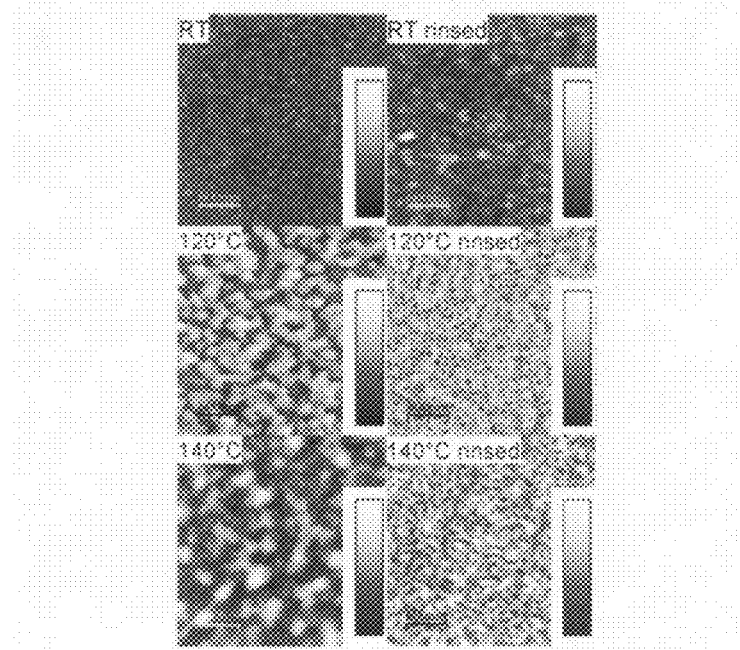
FIG. 24 is atomic force micrographs of layers of compound 4 annealed at various temperatures.

As seen in FIG. 23, annealing temperature had a strong influence of fill factor. For a cell containing P3HT and V-BT, with the highest fill factor and ECE observed after annealing at 140° C. [data for various annealing temperatures: 100° C., 0.61 V, FF=25%, ECE=0.17%; 120° C.: 0.58 V, FF=31%, ECE=0.30%; 140° C.: 0.67 V, FF=37%, ECE=0.45%; 160° C.: 0.65 V, FF=31%, ECE=0.26%.]

During annealing, the compounds crystallize and better percoloation is seen. However, it appears that there is less interfacial area between the donor and acceptor layers and accordingly less exciton dissociation. The surface roughness increased with anealing.

Figure 25:
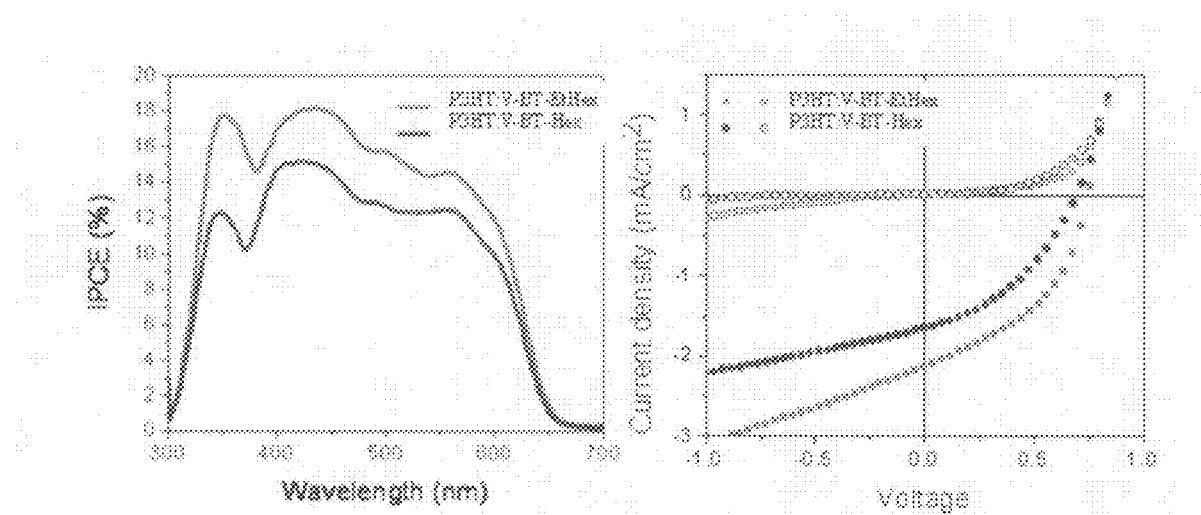
FIG. 25 is IPCE and I(V) curves comparing the effect of ethylhexyl substitution on the imidazole ring compared with hexyl substitution.
Figure 26:
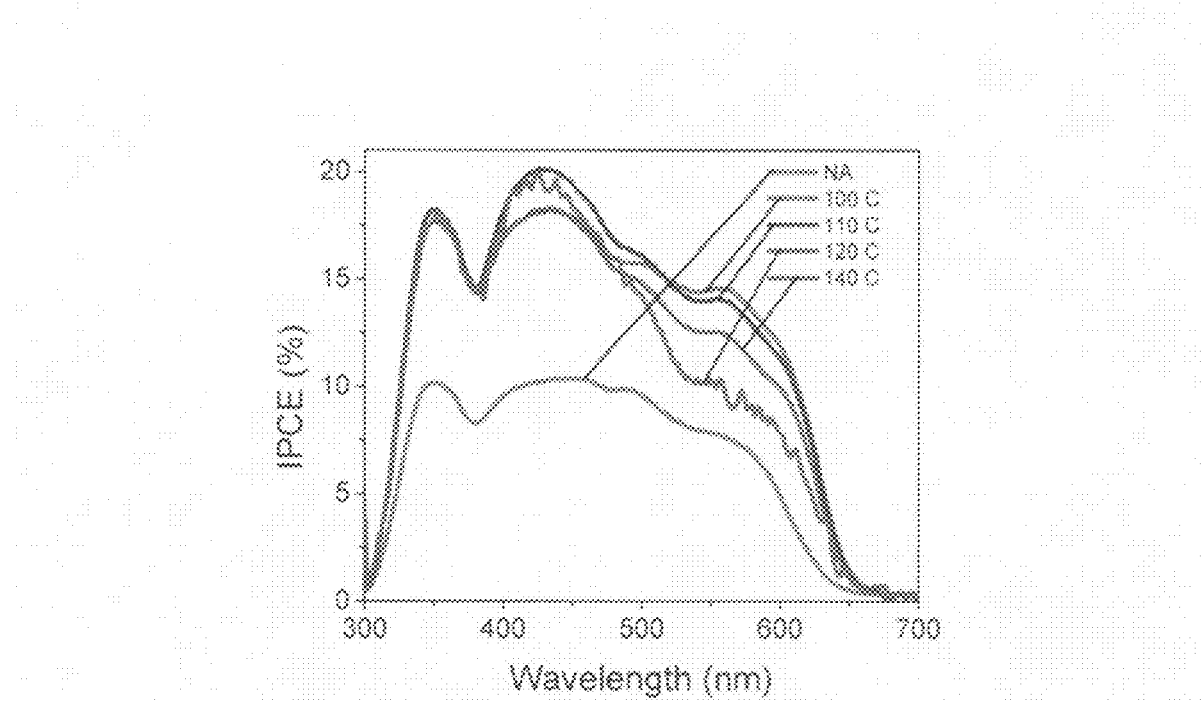
FIG. 26 is IPCE spectra for a device containing P3HT:V-BT-EtHex blend annealed at various temperatures.
Figure 27:
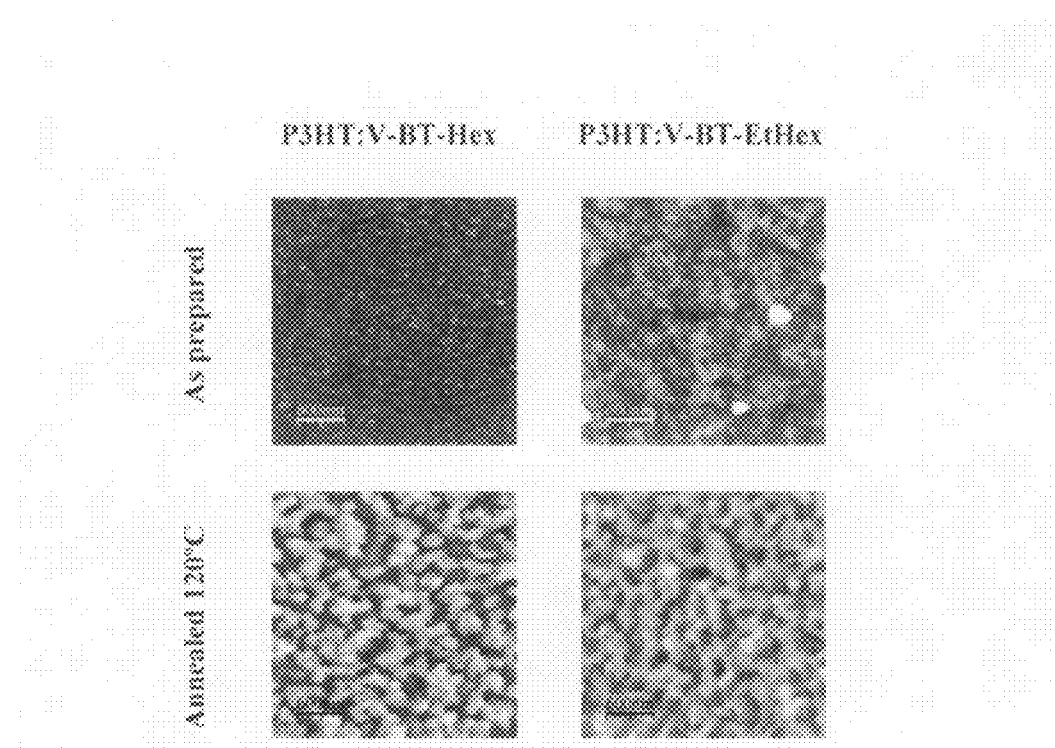
FIG. 27 is atomic force micrographs of layers of P3HT:V-BT-EtHex blend and P3HT:V-BT-EtHex blend.
Figure 28:
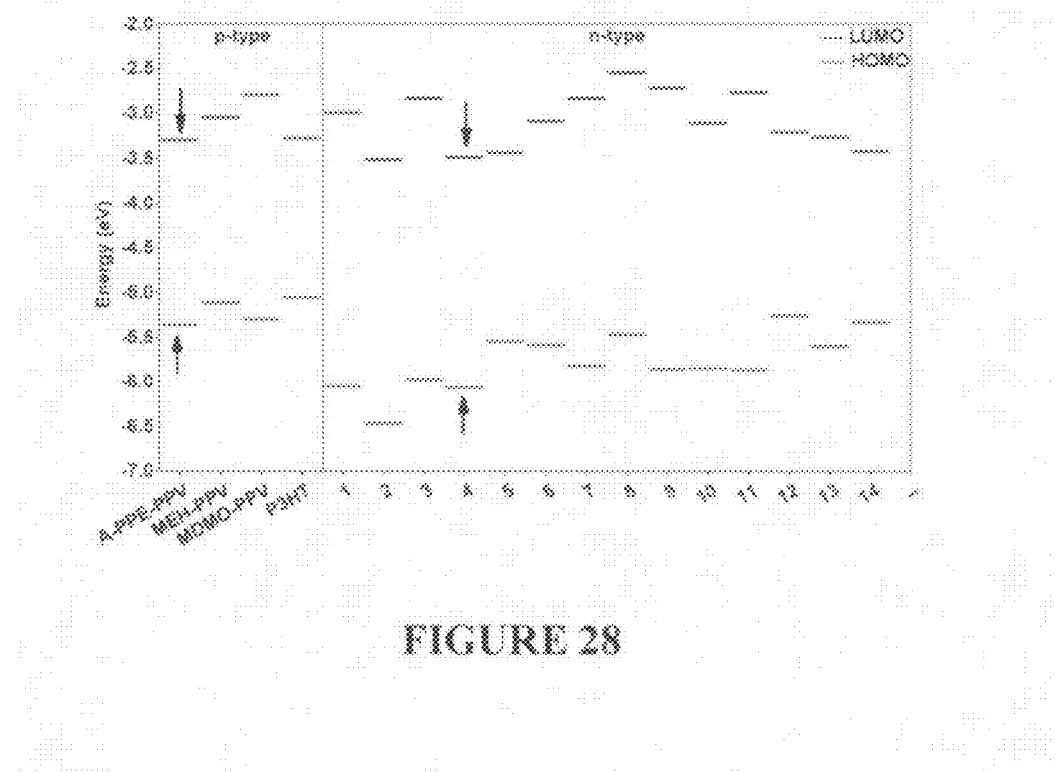
FIG. 28 is a schematic representation of HOMO and LUMO energy level alignment of compounds 1 to 14 with known p-type polymers.

FIG. 25 demonstrates the effect of ethylhexyl derivitization as compared with hexyl derivitization of the imidazole ring. For the ethylhexyl compound 4, the IPCE increased for 15% to 20%, an increase of 33%; the PCE increased from 0.45% to 0.72%, and increase of 60%; and the V$_{oc}$ increased from 0.67 to 0.72 V.

As can be understood by one skilled in the art, many modifications to the exemplary embodiments described herein are possible. The invention, rather, is intended to encompass all such modification within its scope, as defined by the claims.

All documents referred to herein are fully incorporated by reference.

What is claimed is:

1. A compound of formula I:

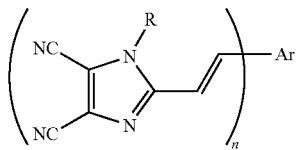

wherein Ar is an aryl or heteroaryl group having from 5 to 100 backbone atoms, R is a C$_1$ to C$_{30}$ branched, unbranched or cyclic alkyl or heteroalkyl group, and n is an integer from 2 to 10.

2. The compound of claim 1, wherein n is equal to 2.

3. The compound of claim 1, wherein Ar comprises one or more of phenyl, nitro-substituted phenyl, alkoxy-substituted phenyl, biphenyl, benzothiadiazolyl, thiophenyl-benzothidiazolyl-thiophenyl, thiophenyl, thienothiophenyl, bithiophenyl, 9,9-dialkylfluorenyl, N-alkylcarbozolyl, dibenzothiophenyl, naphthalyl, binaphthalyl, azulenyl, anthracenyl, tetracenyl, indenyl, pyrenyl and perylenyl.

4. The compound of claim 2, wherein Ar comprises one or more of phenyl, nitro-substituted phenyl, alkoxy-substituted phenyl, biphenyl, benzothiadiazolyl, thiophenyl-benzothidiazolyl-thiophenyl, thiophenyl, thienothiophenyl, bithiophenyl, 9,9-dialkylfluorenyl, N-alkylcarbozolyl, dibenzothiophenyl, naphthalyl, binaphthalyl, azulenyl, anthracenyl, tetracenyl, indenyl, pyrenyl and perylenyl.

5. The compound of claim 2, wherein Ar comprises one or more of:

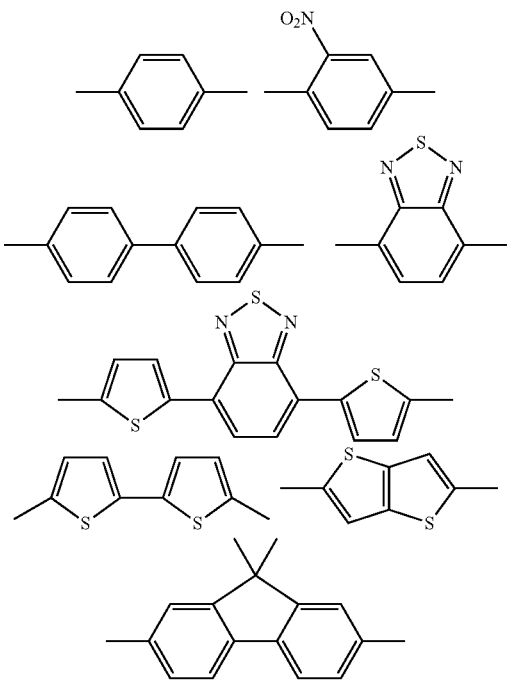

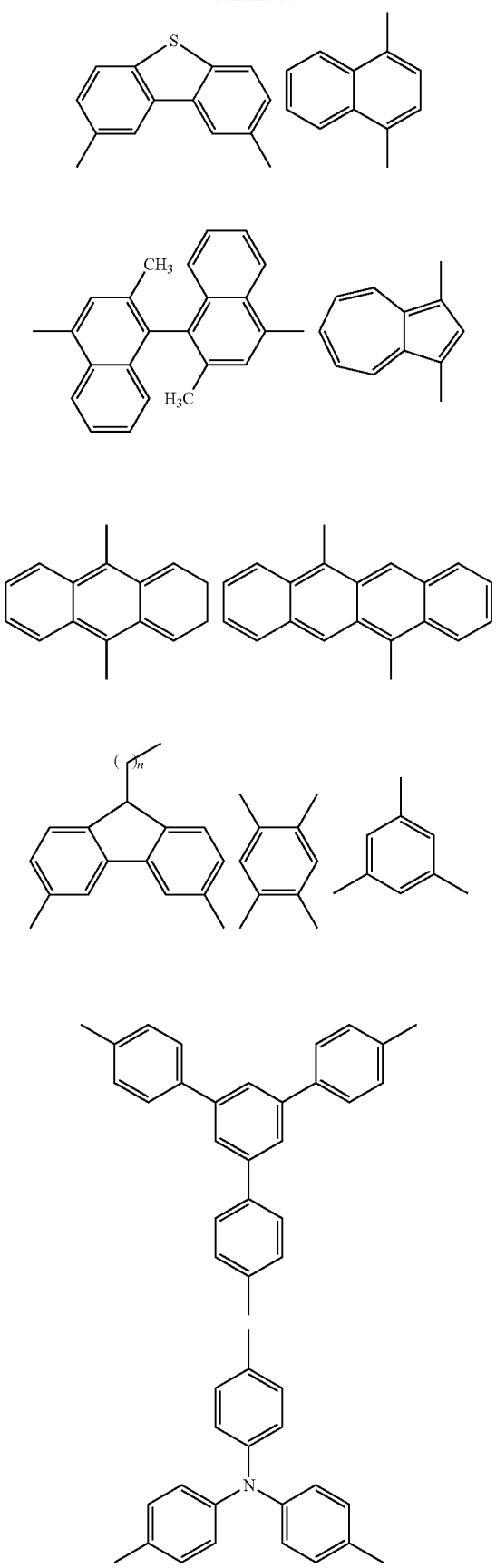
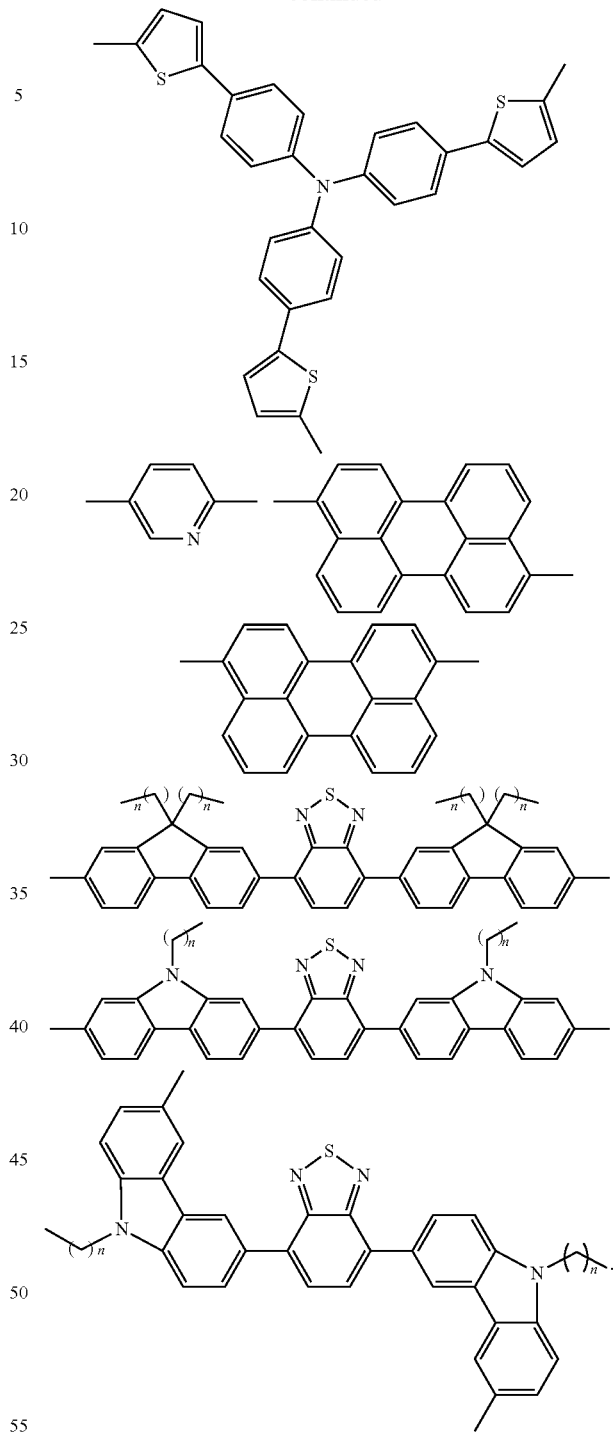
6. The compound of claim 4, wherein Ar comprises benzothiadiazolyl.
7. The compound of claim 1, wherein R comprises one or more of branched hexyl, unbranched hexyl, 2-ethylhexyl, cyclohexylmethyl and fluorinated alkyl.
8. The compound of claim 6, wherein each R independently comprises hexyl or 2-ethylhexyl.

9. A thin film comprising a compound of formula I:

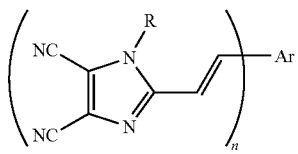

wherein Ar is an aryl or heteroaryl group having from 5 to 100 backbone atoms, R is a $C_1$ to $C_{30}$ branched, unbranched or cyclic alkyl or heteroalkyl group, and n is an integer from 1 to 10.

10. The thin film of claim 9 wherein the thin film is from about 0.1 to about 1000 nm thick.

11. The thin film of claim 9 wherein the thin film further comprises an electron donor material.

12. The thin film of claim 11 wherein the electron donor material comprises regioregular poly(3-hexylthiophene-2,5-diyl) (P3HT), regioregular poly(3-ocylthiophene-2,5-diyl) (P3OT), regioregular poly(quarterthiphene) (PQT), a-poly (phenylene ethynylene)-poly(phenylene vinylene) (A-PPE-PPV), poly[2-methoxy-5-(2'-ethyl-hexyloxy)-1,4-phenylene vinylene] (MEH-PPV), or poly[2-methoxy-5-(3,7-dimethyloctyloxy)-1,4-phenylenevinylene] (MDMO-PPV).

13. The thin film of claim 12 wherein the electron donor material comprises P3HT.

14. A device comprising an anode, a cathode and an electron acceptor material comprising a compound of formula I:

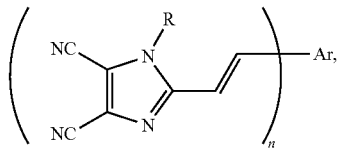

the electron acceptor material disposed between the anode and the cathode, wherein in formula I, Ar is an aryl or heteroaryl group having from 5 to 100 backbone atoms, R is a $C_1$ to $C_{30}$ branched, unbranched or cyclic alkyl or heteroalkyl group, and n is an integer from 1 to 10.

15. The device of claim 14 wherein the electron acceptor material is in a photoactive layer.

16. The device of claim 15 wherein the photoactive layer further comprises an electron donor material.

17. The device of claim 15 wherein the donor material comprises regioregular poly(3-hexylthiophene-2,5-diyl) (P3HT), regioregular poly(3-ocylthiophene-2,5-diyl) (P3OT), regioregular poly(quarterthiophene) (PQT), a-poly (phenylene ethynylene)-poly(phenylene vinylene) (A-PPE-PPV), poly[2-methoxy-5-(2'-ethyl-hexyloxy)-1,4-phenylene vinylene] (MEH-PPV), or poly[2-methoxy-5-(3,7-dimethyloctyloxy)-1,4-phenylenevinylene] (MDMO-PPV).

18. The device of claim 15 wherein the photoactive layer is from about 0.1 to about 1000 nm thick.

19. The device of claim 15 wherein the photoactive layer further comprises an electron donor material comprising P3HT.

20. The device of claim 14 further comprising a smoothing layer disposed between the electron acceptor material and the anode, or between the electron acceptor material and the cathode.

21. The device of claim 20 wherein the smoothing layer is disposed between the electron acceptor material and the anode and comprises a mixture of PEDOT and PSS.

22. The device of claim 20 wherein the smoothing layer is disposed between the electron acceptor material and the cathode and comprises calcium.

23. The device of claim 14 wherein the anode comprises gold, silver, fluorine tin oxide, indium tin oxide or a conductive polymer.

24. The device of claim 23 wherein the anode comprises indium tin oxide.

25. The device of claim 14 wherein the cathode comprises barium, calcium, magnesium, indium, aluminum, ytterbium, silver, a calcium:silver alloy, an aluminum:lithium alloy, or a magnesium:silver alloy.

26. The device of claim 25 wherein the cathode comprises silver.

27. A method of synthesizing a compound according to claim 1, comprising:
reacting 1-R-vinzene with a bromoaromatic compound in the presence of a palladium catalyst and a base,
wherein the bromoaromatic compound has from 5 to 100 backbone atoms and R is a $C_1$ to $C_{30}$ branched, unbranched or cyclic alkyl or heteroalkyl group, whereby a compound represented by formula I according to claim 1 is formed.

28. The method of claim 27 wherein the bromoaromatic compound is a dibromoaromatic compound.

29. The method of claim 28 wherein the dibromoaromatic compound comprises 1,4-dibromobenzene, 1,4-dibromo-2-nitrobenzene, 4,4'-dibromobiphenyl, 4,7-dibromo-2,1,3-benzothiadiazole, 4,7-bis(5-bromo-2-thienyl)-2,1,3-benzothiadiazole, 5,5'-dibromo-2,2'-bithiophene, 2,7-dibromo-9,9'-dimethylfluorene, N-hexyl-3,6-dibromocarbazole, 3,6-dibromo-dibenzothiophene, 1,4-dibromonaphthalene, 4,4'-dibromo-2,2'-dimethyl-1,1'-binaphthalyl, 1,3-dibromoazulene, 9,10-dibromoanthracene or 5,11-dibromotetracene.

30. The method of claim 28 wherein the dibromoaromatic compound comprises 4,7-dibromo-2,1,3-benzothiadiazole.

31. The method of claim 27 wherein 1-R-vinazene comprises one or more of 1-hexylvinazene, 1-2-ethylhexylvinazene or 1-cyclohexylmethylvinazene.

32. The method of claim 27, wherein the palladium catalyst comprises bis(tri-t-butylphosphine)-palladium(0).

33. The method of claim 27, wherein the base comprises dicyclohexylmethylamine.

* * * * *